United States Patent [19]

Bentley et al.

[11] Patent Number: 4,863,959

[45] Date of Patent: Sep. 5, 1989

[54] ANTHRANILONITRILE DERIVATIVES AS USEFUL AGENTS FOR PROMOTING GROWTH, IMPROVING FEED EFFICIENCY, AND FOR INCREASING THE LEAN MEAT TO FAT RATIO OF WARM-BLOODED ANIMALS

[75] Inventors: Terence J. Bentley, East Windsor; Goro Asato, Titusville, both of N.J.

[73] Assignee: American Cyanamid Company, Stamford, Conn.

[21] Appl. No.: 910,026

[22] Filed: Sep. 24, 1986

Related U.S. Application Data

[63] Continuation-in-part of Ser. No. 879,867, Jun. 27, 1986, abandoned, which is a continuation-in-part of Ser. No. 788,298, Oct. 17, 1985, abandoned.

[51] Int. Cl.4 ............... A01K 31/275; A01K 31/135; C07C 87/28; C07C 121/52
[52] U.S. Cl. .................................... 514/524; 514/649; 558/422; 564/363
[58] Field of Search ............... 514/524, 649; 558/422; 564/363

[56] References Cited

U.S. PATENT DOCUMENTS 4,407,819 10/1983 Kiernan et al. .................... 514/524

FOREIGN PATENT DOCUMENTS 0026298 4/1981 European Pat. Off. .
0049728 4/1982 European Pat. Off. .
0103830 3/1984 European Pat. Off. .
2210414 7/1974 France .
1178191 1/1970 United Kingdom .

OTHER PUBLICATIONS

G. Asato et al., "Agricultural Biol. Chem.", vol. (11):, 2883-2888, (1984).
Keck et al., "Arzneim-Forsch," vol. 22, No. 5, (1972), pp. 861-869.

Primary Examiner—Anton H. Sutto
Attorney, Agent, or Firm—Alice C. Brennan

[57] ABSTRACT

There are provided novel anthranilonitrile derivatives and related compounds which are useful for promoting growth, improving feed efficiency and for increasing the lean meat to fat ratio of warm-blooded animals.

33 Claims, No Drawings

ANTHRANILONITRILE DERIVATIVES AS USEFUL AGENTS FOR PROMOTING GROWTH, IMPROVING FEED EFFICIENCY, AND FOR INCREASING THE LEAN MEAT TO FAT RATIO OF WARM-BLOODED ANIMALS

This application is a continuation-in-part of application Ser. No. 879,867, filed June 27, 1986, abandoned, which is a continuation-in-part of application Ser. No. 788,298, filed Oct. 17, 1985, abandoned.

BACKGROUND OF THE INVENTION

Phenylethanolamines illustrated by the structure:

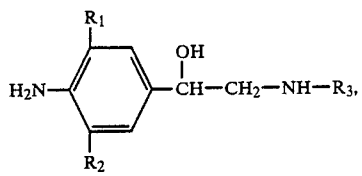

wherein $R_1$ is H, halo or CN; $R_2$ is F, $CF_3$, $NO_2$ or CN and $R_3$ represents a variety of substituents, such as ($C_3$–$C_5$) alkyl and ($C_3$–$C_5$) cycloalkyl; are reported in U.S. Pat. No. 4,119,710 as analgesics, uterospasmolytics, bronchospasmolytics and antispastics for the skeletal musculature, and especially as $\beta_2$-receptor mimetics and $\beta_1$-receptor blockers. Other related dihaloamino- and monohaloamino-phenylethanolamine compounds with similar biological activity are disclosed in U.S. Pat. Nos. 3,536,712 and 3,574,211.

In U.S. Pat. No. 4,407,819, many of the above said compounds as well as a variety of other phenylethanolamine derivatives are described as agents useful for increasing lean meat deposition and/or improving the lean meat to fat ratio of warm-blooded animals, such as swine, poultry, sheep, goats, cattle and domestic pets.

Still other phenylethanolamine derivatives are disclosed in U.S. Pat. No. 4,404,222 and are said to be agents useful for increasing the growth rate of meat producing animals and improving the efficiency of feed utilization thereby.

Recently, Offenlegungsschrift DE No. 3,306,159 A1 (European Patent Application No. 103830) was published describing substituted phenylethylamine derivatives which were said to be growth promoters for pigs, cows, poultry, cats, dogs, rabbits, fur animals, fish, and reptiles.

In a pending U.S. patent application Ser. No. 714,240, 3-[(2-tert-butylamino)-1-hydroxyethyl]-5-fluorobenzonitrile and 3-fluoro-5-[1-hydroxy-2-(isopropylamino)ethyl]benzonitrile were also described as new compounds for increasing the lean meat to fat ratio and/or improving the efficiency of feed utilization, and/or enhancing the growth rate of warm-blooded animals.

While the above-said phenylethanolamine derivatives demonstrate utility for the purposes described, it would be advantageous if still other new compounds could be found that are more potent for increasing the lean meat to fat ratio of meat producing animals, improving the growth rate thereof and/or enhancing the efficiency of feed utilization thereby. It would also be especially advantageous if the novel phenylethanolamines would exhibit less $\beta_1$ heart stimulant activity and would shown an improved margin of safety over the known phenylethanolamines and would not be subject to residue retention in the animal tissues.

SUMMARY OF THE INVENTION

The novel anthranilonitrile compounds and related compounds of this invention are depicted by formula I below:

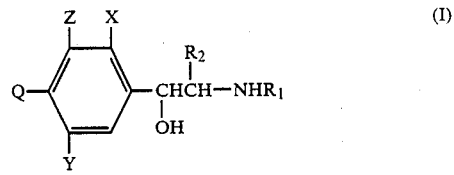

wherein $R_1$ is ethyl, n-propyl, isopropyl, tert-butyl, 2-butyl, cyclobutyl or cyclopentyl; $R_2$ is hydrogen or methyl; X is fluorine or chlorine; Y is hydrogen, methyl, fluorine, chlorine or bromine; Z is hydrogen, fluorine, chlorine or cyano; Q is hydrogen or $NR_3R_4$; where $R_3$ and $R_4$ are each independently hydrogen, methyl, ethyl, n-propyl or isopropyl; with the provisos that Y and Z cannot simultaneously be hydrogen; that when Y is hydrogen, X and Z cannot be chlorine; that when Q is hydrogen, Z is cyano; and that when Z is hydrogen, X is fluorine and Y is fluorine or chlorine; the optical isomers; and the pharmacologically acceptable salts thereof.

The substituted anthranilonitrile derivatives and related compounds of the invention are surprisingly effective agents for promoting growth, improving feed efficiency and more potent for increasing the lean meat to fat ratio of warm-blooded animals. These anthranilonitrile derivatives and related compounds have the advantage that they exhibit more potent activity in reducing fat than many of their predecessors and/or in promoting growth. In addition, they may be readily eliminated by the animals receiving them and thus, their administration at very low levels results in small or negligible levels of the anthranilonitrile and related compounds in edible tissues.

The compounds of this invention are also potentially useful as antiasthmatics and antiobesity agents for humans, especially the compounds of the invention that lack an amine function in the benzene ring.

Unexpectedly, the introduction of a halo substituent in the ortho position relative to the ethanolamine side chain of a polysubstituted phenylethanolamine, depending on the group adjacent to this halo group, significantly improves potency over prior art compounds and the above pending U.S. patent application.

DESCRIPTION OF THE PREFERRED EMBODIMENTS

The compounds of the present invention are prepared by reacting essentially equimolar amounts of 3-fluoroacetanilide with aluminum chloride in the presence of acetyl chloride to yield 2-fluoro-4-acetamidoacetophenone. Hydrolysis of the 2-fluoro-4-acetamidoacetophenone, with aqueous mineral acid, such as hydrochloric acid, in the presence of a lower alkyl aliphatic alcohol, such as methanol, affords 4-amino-2-fluoroacetophenone which is readily brominated with N-bromosuccinimide, preferably in the presence of an inert organic solvent, such as dichloromethane. The reaction yields a mixture of 4-amino-3-bromo- 2-fluoroacetophenone and 4-amino-3-bromo-6-fluoroacetophenone.

The 4-amino-3-bromo-2-fluoroacetophenone is then treated with cuprous cyanide in the presence of a non-protic solvent, such as dimethylformamide, at an elevated temperature between about 100° and 175° C. and preferably under a blanket of inert gas such as nitrogen. The reaction mixture is then cooled and treated with aqueous sodium cyanide solution to afford 4-amino-3-cyano-2-fluoroacetophenone. Treatment of the above-said acetophenone with cupric bromide and ethyl acetate at refluxing temperature, between about 75° and 150° C. for about one to two hours, yields the 5-(bromoacetyl)-fluoroanthranilonitrile which is readily converted to 5-[2-(tert-butylamino)-1-hydroxyethyl]-6-fluoroanthranilonitrile by reaction with tert-butyl amine under a blanket of inert gas, such as nitrogen. The reaction is preferably conducted in the presence of a lower alkyl ($C_1$–$C_4$) aliphatic alcohol and a reducing agent, such as sodium borohydride.

Similarly, reaction of 5-(bromoacetyl)-6-fluoro-anthranilonitrile with the appropriate ($C_2$–$C_4$) alkylamine or ($C_4$–$C_5$) cycloalkylamine, depicted by the formula $R_1NH_2$ wherein $R_1$ is as defined above in the presence of a lower alkyl aliphatic alcohol and sodium borohydride yields the anthranilonitrile having the structure:

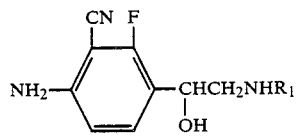

wherein $R_1$ is ethyl, n-propyl, isopropyl, t-butyl, 2-butyl, cyclobutyl or cyclopentyl.

These reactions are graphically illustrated in Flow Diagram I below.

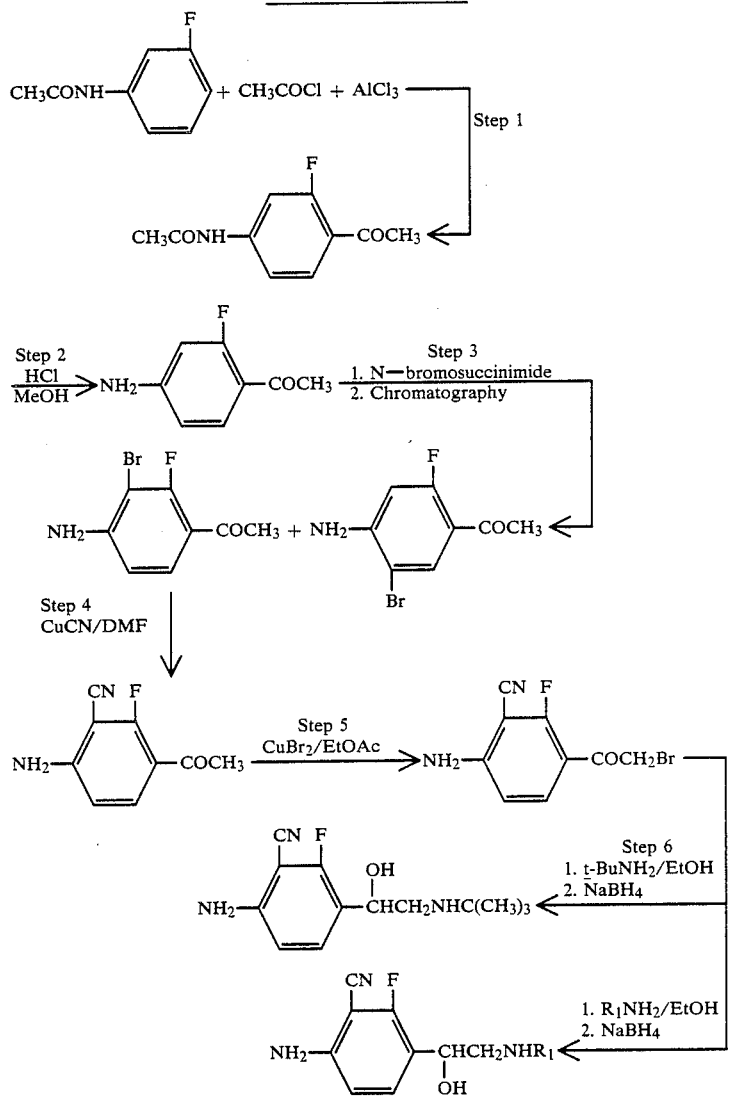

Preparation of 5-[2-(alkylamino)-1-hydroxyethyl]-6-fluoro-N-alkylanthranilonitrile and/or 5-[2-(alkylamino)-1-hydroxyethyl]-6-fluoro-N,N-dialkylanthranilonitrile is achieved by dissolving 5-[2-(alkylamino)-1-hydroxyethyl]-6-fluoroanthranilonitrile in an excess of $C_1$–$C_3$ alkanoic acid and sodium borohydride or sodium cyanoborohydride. If the reaction mixture is maintained at a temperature between about 5° and 20° C. for from one to several hours, the reaction yields a mixture of the 5-[2-(alkylamino)-1-hydroxyethyl]-6-fluoro-N-alkylanthranilonitrile and the 5-[2-(alkylamino)-1-hydroxyethyl]-6-fluoro-N,N-dialkylanthranilonitrile which can be separated by chromatography.

Where it is desirable to obtain a product in which the alkyl groups in the N,N-dialkyl function of the N,N-dialkylanthranilonitrile are different, the N-monoalkylated anthranilonitrile, obtained as described above, can be reductively alkylated in an excess of the appropriate alkanoic acid having the desired alkyl chain length and sodium cyanoborohydride, sodium borohydride or the like. The temperature of the reaction mixture is maintained at from about 5° to 20° C. for from about one to four hours.

To obtain a 5-[2-(alkylamino)-1-hydroxyethyl]-6-fluoro-N,N-dialkylanthranilonitrile in which the N,N-dialkyl functions are the same, the appropriate 5-[2-(alkylamino)-1-hydroxyethyl]-6-fluoroanthranilonitrile is dissolved in an excess of an alkanoic acid having a chain length which will provide the desired N,N-dialkyl function. To this solution is added sodium borohydride and the mixture is then heated to a temperature between about 25° and 70° C. for from about 2 to 50 hours.

These reactions are graphically illustrated in Flow Diagram II below.

FLOW DIAGRAM II

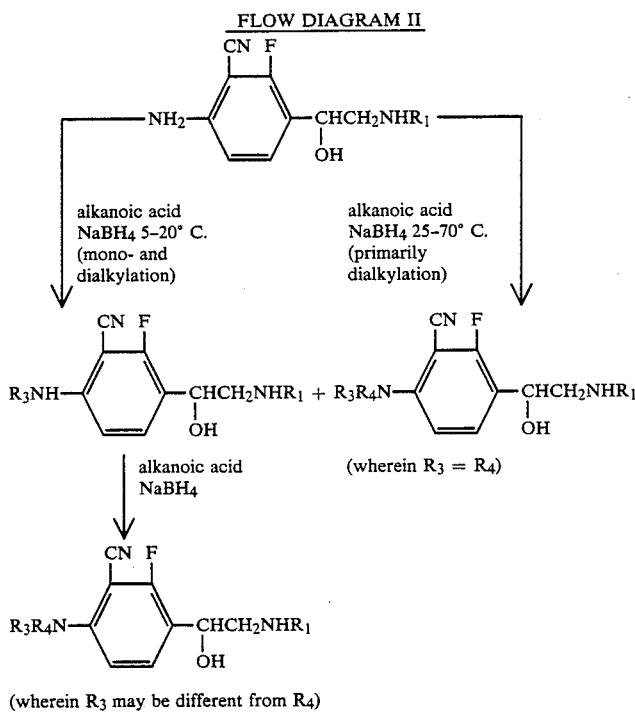

(wherein $R_3$ may be different from $R_4$)

Anthranilonitriles of formula I having a methyl function at $R_2$ are prepared in essentially the same manner as described for the preparation of formula I compounds in which $R_2$ represents hydrogen. The primary difference between the reactions occurs in the initial reaction wherein propionyl chloride is substituted for acetyl chloride and the resulting phenone is 2-fluoro-4-acetamidopropiophenone rather than 2-fluoro-4-acetamidoacetophenone. Since the reactions and reaction conditions for the preparation of the formula I anthranilonitriles in which $R_2$ is methyl, follow the description for formula I compounds wherein $R_2$ is hydrogen, the process for the preparation of formula I compounds in which $R_2$ is methyl is simply illustrated in Flow Diagram III below.

FLOW DIAGRAM III

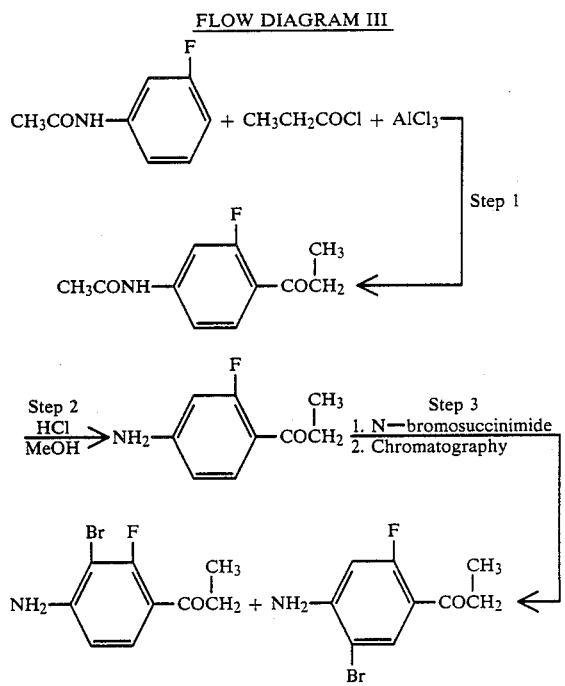

-continued
FLOW DIAGRAM III
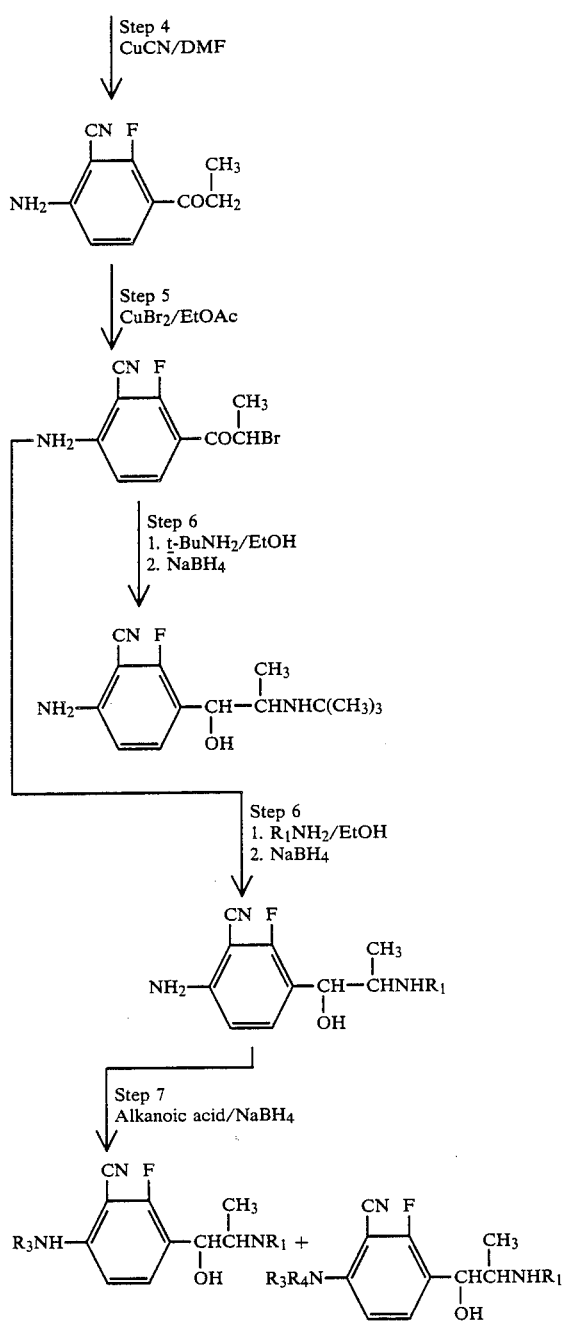
Other related compounds of this invention are prepared by similar methods that are graphically illustrated in flow diagrams IV to X.
FLOW DIAGRAM IV

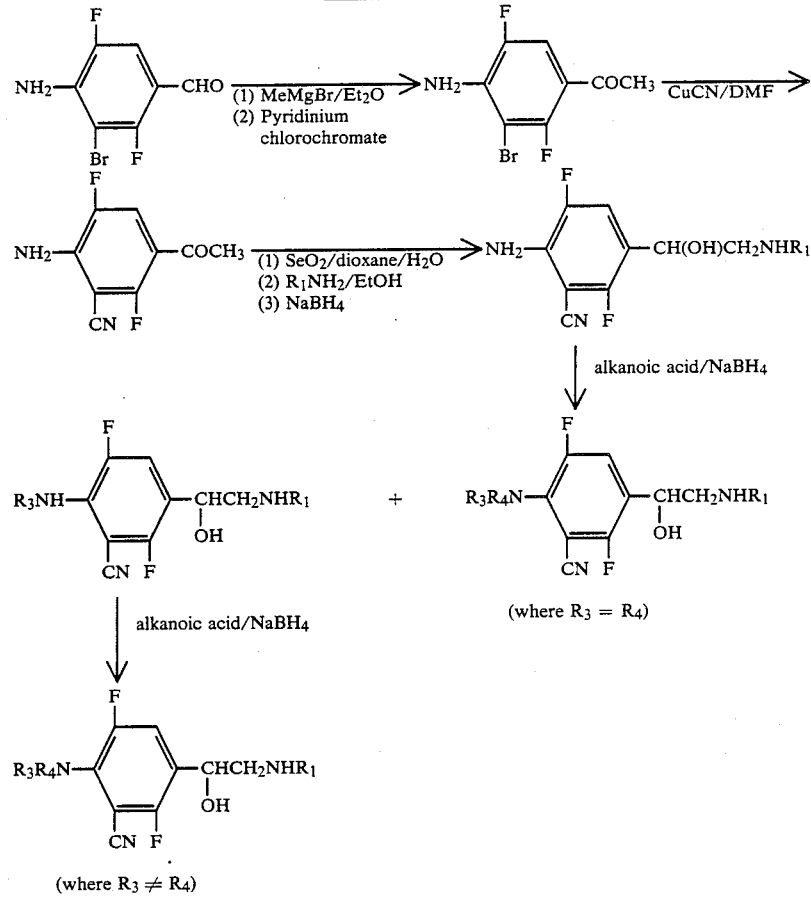
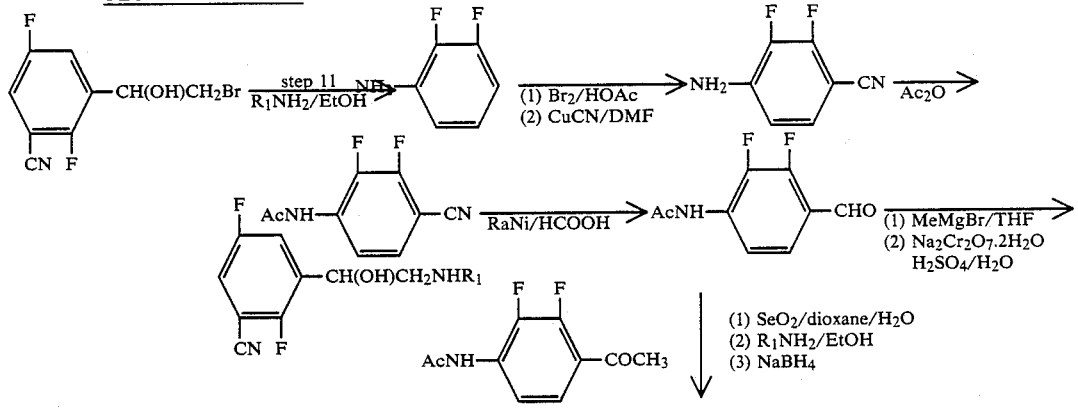

-continued
FLOW DIAGRAM VI
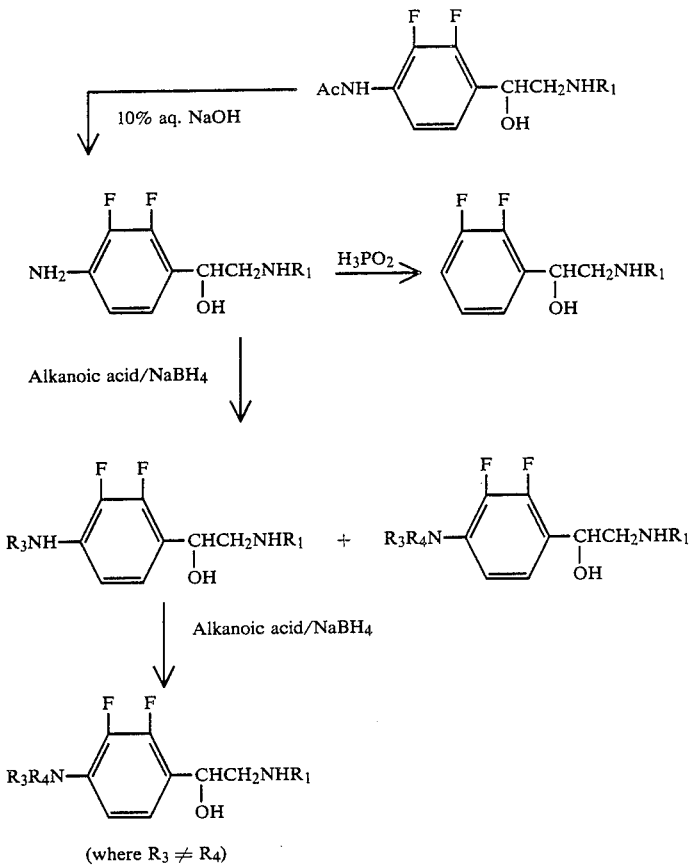
FLOW DIAGRAM VII
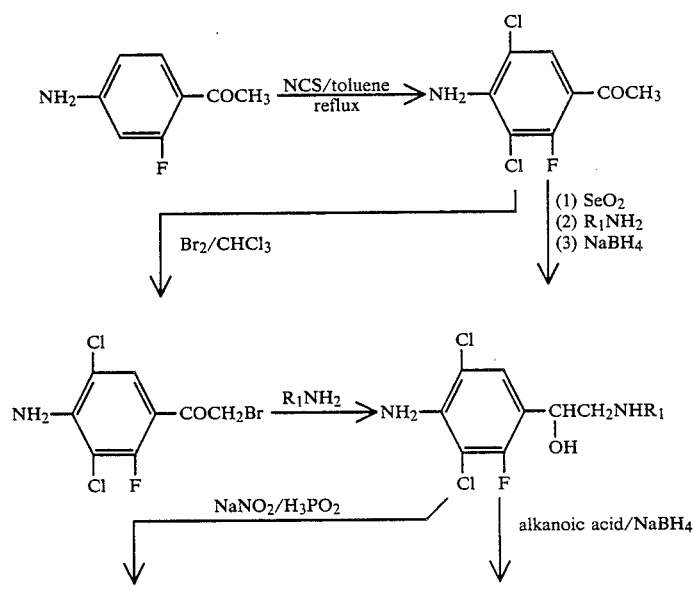

FLOW DIAGRAM VII
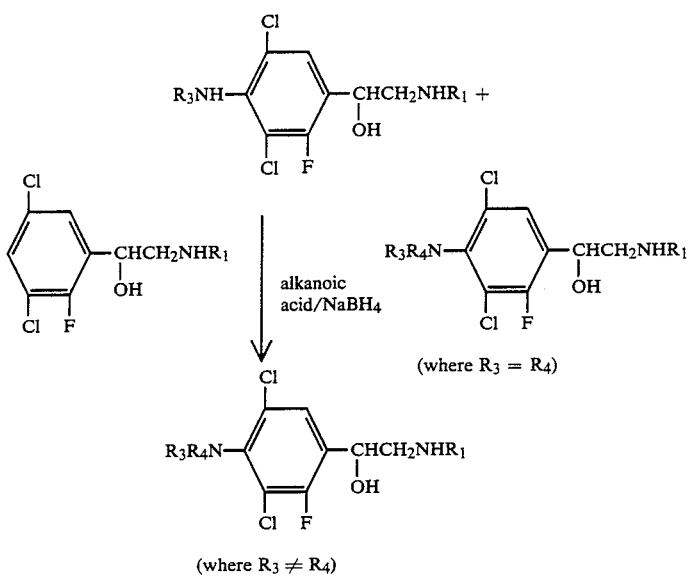
FLOW DIAGRAM VIII
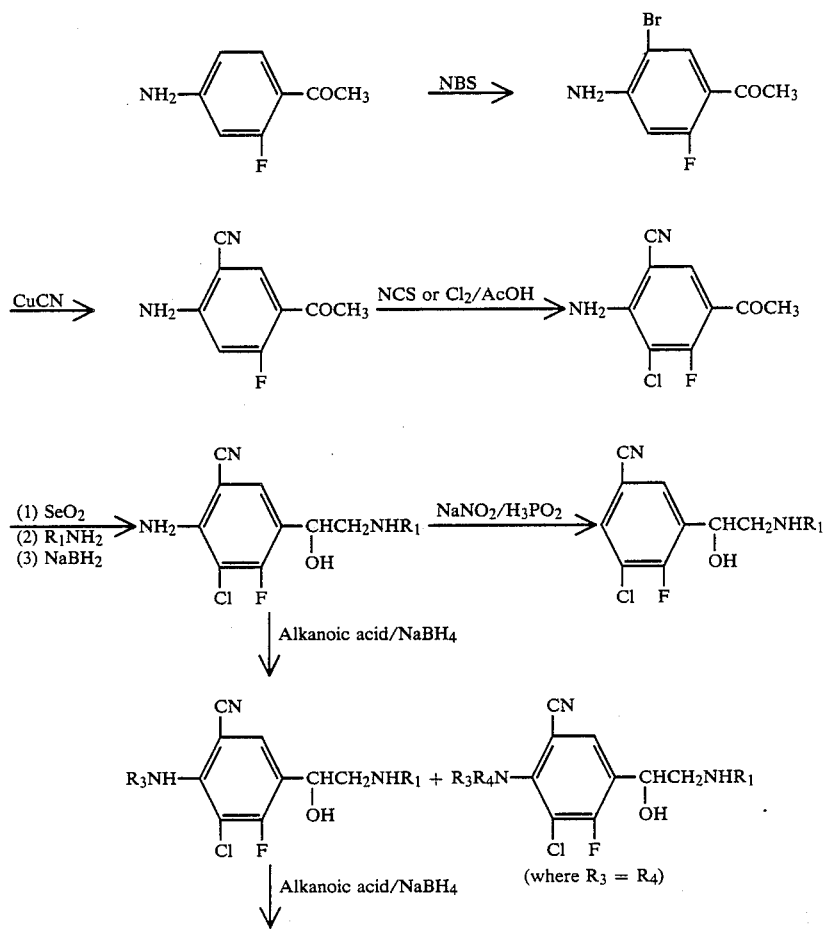

FLOW DIAGRAM VIII
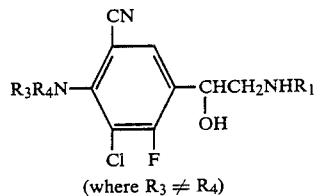
(where R₃ ≠ R₄)
FLOW DIAGRAM IX
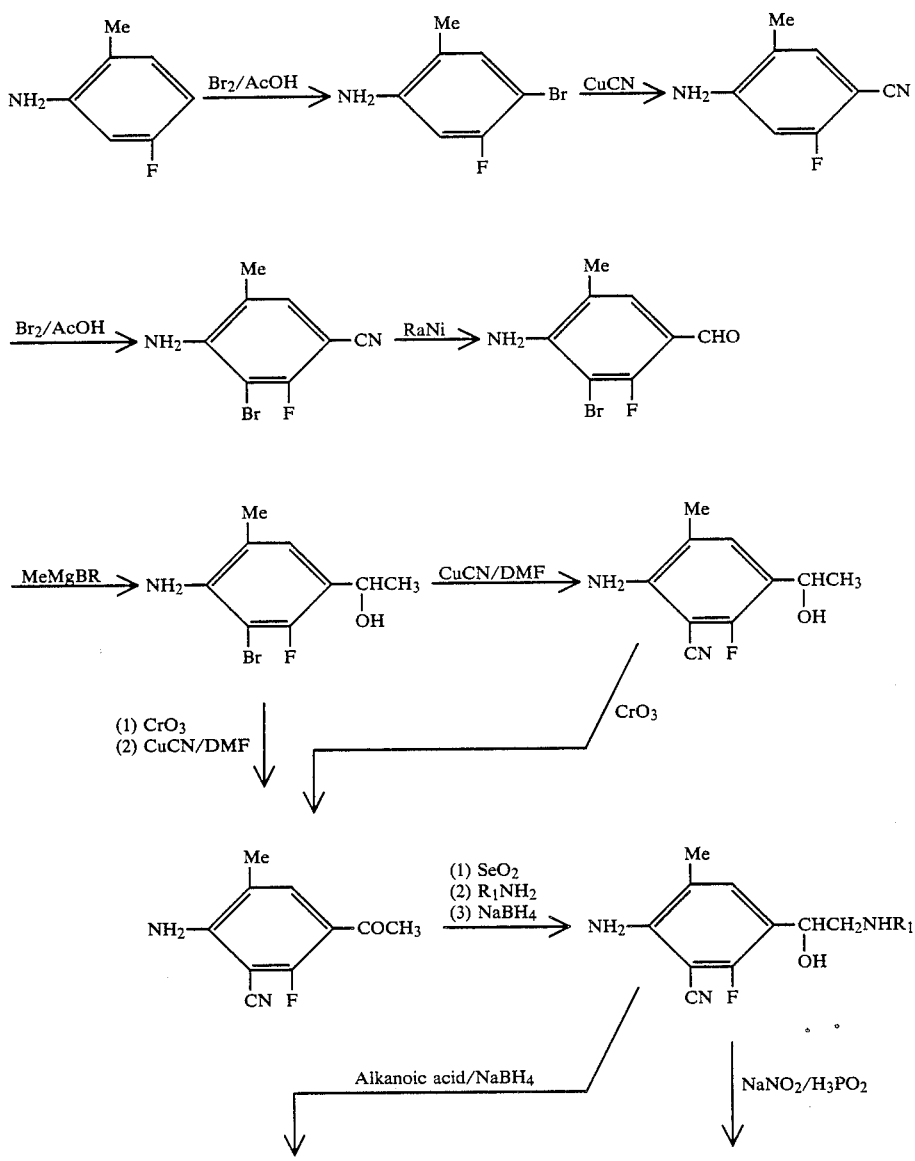

-continued
FLOW DIAGRAM IX
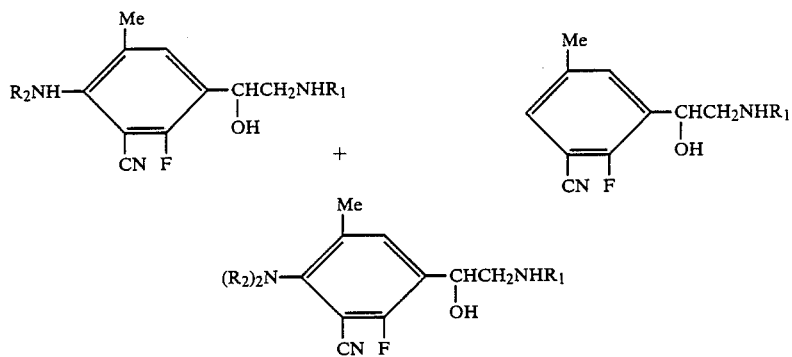
FLOW DIAGRAM X
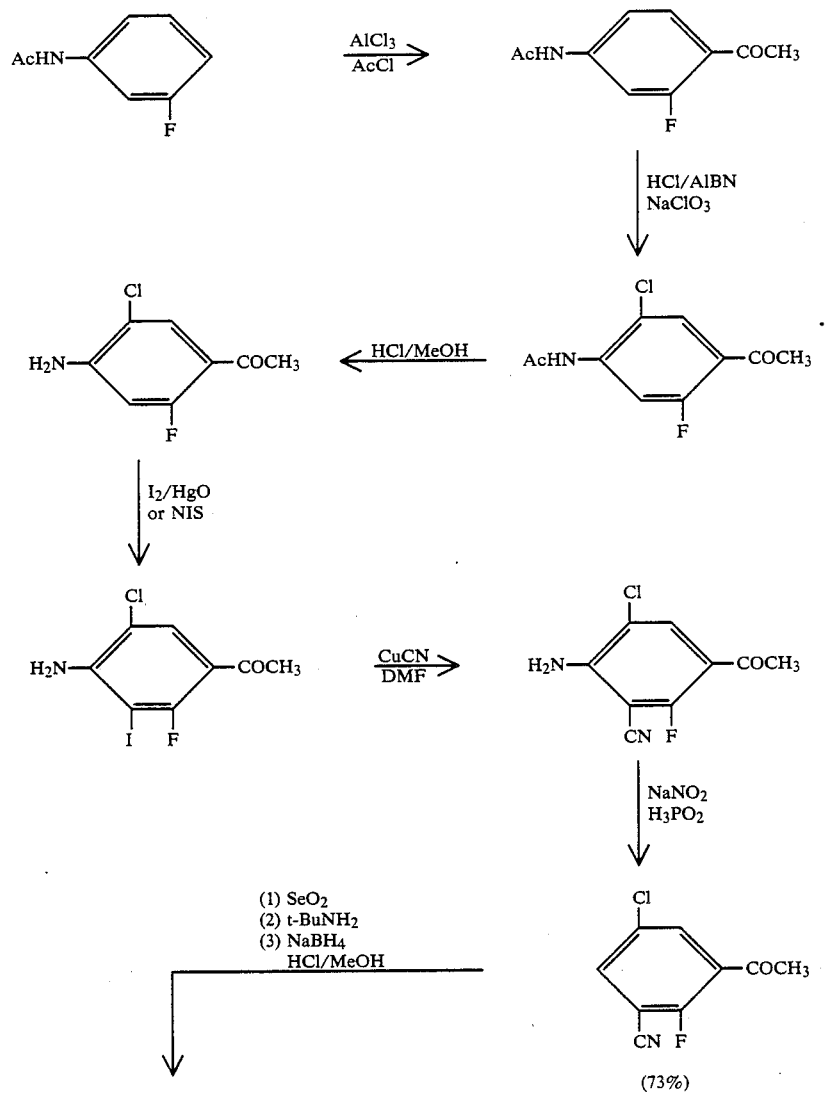

FLOW DIAGRAM X

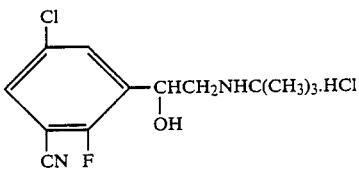

-continued

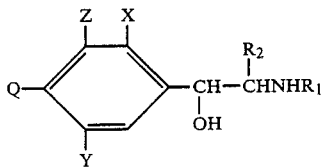

The methodologics depicted in flow diagrams I to X are also used in preparing other novel compounds of this invention and are readily put to practice by one skilled in the art with minor and obvious modifications.

In accordance with the invention, it has been found that an increase in animal growth rate, an improvement in the efficiency of feed utilization by meat-producing animals and domestic pets and an improvement in the carcass quality of meat-producing animals, i.e. increased lean meat to fat ratio, is achieved by administering to said animals an effective amount of a compound having the following structure:

wherein $R_1$ is ethyl, n-propyl, isopropyl, tert-butyl, 2-butyl, cyclobutyl or cyclopentyl; $R_2$ is hydrogen or methyl; X is fluorine or chlorine; Y is hydrogen, methyl, fluorine, chlorine or bromine; $Z$ is hydrogen, fluorine, chlorine or cyano; and Q is hydrogen or $NR_3R_4$; where $R_3$ and $R_4$ are each independently hydrogen, methyl, ethyl, n-propyl or isopropyl; with the provisos that Y and $Z$ cannot simultaneously be hydrogen; and when $Z$ is hydrogen, Y is fluorine or chlorine and X is fluorine; the optical isomers; and the pharmaceutically acceptable salts thereof.

A preferred group of compounds have the above structure wherein $R_2$ is hydrogen; Y is hydrogen, methyl, fluorine or chlorine; and where $R_1$, X, $Z$, Q, $R_3$ and $R_4$ are as defined above with the provisos; the optical isomers, and the pharmacologically acceptable salts thereof.

Another preferred group of compounds have the above structure wherein $R_2$ is hydrogen; Y is hydrogen, fluorine or chlorine; and where $R_1$, X, $Z$, Q, $R_3$ and $R_4$ are as defined above with the provisos; the optical isomers and the pharmacologically acceptable salts thereof.

Still another preferred group of compounds have the above structure wherein $R_1$ is isopropyl or tert-butyl; $R_2$ is hydrogen; Y is hydrogen, fluorine or chlorine; and where X, $Z$, Q, $R_3$ and $R_4$ are as defined above with the provisos; the optical isomers; and the pharmacologically acceptable salts thereof.

A most preferred group of compounds the above structure wherein $R_1$ is isopropyl or tert-butyl; $R_2$ is hydrogen; Y is hydrogen, fluorine or chlorine; Q is hydrogen or $NH_2$; X and Z are as defined above with the provisos; the optical isomers; and the pharmacologically acceptable salts thereof.

Other $R_1$ groups may also be incorporated into these 2-halosubstituted compounds of this invention and generally tertiary or secondary carbon attachment to the nitrogen is preferred for useful activity.

The anthranilonitrile derivatives and related compounds of the invention can be administered either orally or parenterally to meat-producing animals and domestic pets. The active compounds may be mixed directly with animal feeds or, preferably, prepared in the form of an animal-feed premix, animal-feed concentrate, or feed supplement which can be blended with the feed or applied as a top dressing thereto. The anthranilonitrile derivatives and related compounds may also be administered as subcutaneous implants under the skin of the animals head or ears in the form of pellets, gels or pastes.

When the anthranilonitrile derivatives and/or related compounds of the invention are to be utilized in or with an animal's daily ration, it is usually preferably to prepare the derivatives in the form of an animal feed premix or concentrate that is blended with the feed in sufficient quantity to provide from 0.05 to 200 ppm of active ingredient or preferably 0.05 to 100 ppm of active ingredient in total feed. If the premix is used as a top dressing, enough premix should be spread over the feed to provide from 0.05 to 200 ppm and preferably 0.05 to 100 ppm of active ingredient based on the total feed.

Animal-feed premixes, supplements or concentrates are readily prepared by mixing, on a weight basis, about 5.0 to 50% of an anthranilonitrile derivative or related compound or pharmacologically acceptable salt thereof, with about 50 to 95.0% of an edible diluent. Diluents suitable for use in the manufacture of animal-feed supplements, concentrates, and premixes include: corn meal, fish meal, soybean meal, bone meal, alfalfa meal, cottonseed oil meal, urea, molasses and other similar materials. Use of the diluents in feed supplements, concentrates and premixes improves uniformity of distribution of the active ingredients in the finished feed.

Feed for swine, cattle, sheep and goats generally contain about 0.05 to 200 grams of active ingredient per ton of feed with an optimum level of about 0.125 to 200 grams of active ingredient per ton of feed. Poultry and domestic-pet feeds are usually prepared in such a manner as to contain from about 0.05 to 100 grams and most preferably about 0.1 to 100 grams of active ingredient per ton of feed.

For parenteral administration of the active ingredient, the formula I anthranilonitrile or related compound or pharmaceutically acceptable salt thereof, is formulated as a pellet, paste or gel and administered to the animals by subcutaneous injection. This procedure involved injection of a sufficient number of pellets or a sufficient amount of the formulated paste or gel containing the antranilonitrile derivative or related compound to provide the animals with about 0.001 to 100 mg/kg of body weight/day of said compound.

The preferred dosage for swine, cattle, sheep and goats ranges from about 0.001 to 50 mg/day/kg of body weight of the formula I anthranilonitrile or related compound or pharmacologically acceptable salt thereof. The preferred dosage of the formula I compound for poultry and domestic pets ranges from about 0.001 to 10 mg/day/kg of animal body weight.

Paste or gel formulations suitable for subcutaneous injection can be prepared by dispersing a formula I anthranilonitrile derivative or related compound or pharmacologically acceptable salt thereof in a pharmacologically acceptable diluent, such as propylene glycol, peanut oil, corn oil or an aqueous, thermally reversible, gel composition.

A typical gel formulation can be prepared in accordance with the following procedure.

The gellant phase is prepared by slurrying the gellant 15% to 50% and preferably 15% to 35% by weight of formulation in propylene glycol 14% to 30% by weight for 15 minutes to one hour under reduced pressure 25 to 50 mm Hg at room temperature. The gellant selected is a nonionic surfactant of structure α-hydro-Ω-hydroxy-poly(oxyethylene)poly(oxypropylene)poly(oxyethylene) block copolymer, average molecular weight 12,500; mp 56° C.; Brookfield viscosity of 3,100 at 77° C.; surface tension of a 0.1% aqueous solution: 40.6 dynes/cm (measured with a duNouy tensiometer).

An aqueous solution containing the remaining ingredients may then be prepared by dissolving or dispersing the Formula I anthranilonitrile or related compound or an acceptable salt thereof, in amounts of from about 3% to about 25% by weight and preferably 6% to 12% by weight of final formulation in deionized or distilled water used in amounts of from about 15% by weight to about 50% by weight and preferably 35% to 45% by weight of formulation. This solution is buffered by dissolving 1.5% by weight of citric acid and 1.0% by weight of trisodium citrate to provide a pH range at which long-term chemical stability of the components is achieved, i.e., pH 3-3.5.

Optional components, which may be incorporated into the above solution at this stage are:

a. Benzyl alcohol added in amounts of from about 0.5% by weight to about 1.5% by weight and preferably 1.5% by weight of formulation as an antimicrobial preservative;

b. The yellow dye C.I. Acid yellow No. 23, ("tartrazine," F. D. & C yellow No. 5; 4,5-dihydro-5-oxo-1-(4-sulfophenyl)-4-[(sulfophenyl)azo]-1H-pyrazole-3-carboxylic acid trisodium salt) used as a coloring agent in amounts of from about 0.01% by weight to about 0.03% by weight and preferably 0.01% by weight of formulation;

c. An antifoaming agent comprising a mixture of dimethylpolysiloxanes of structure:

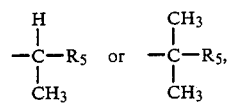

and silica gel, wherein the calculated average value of m is 200 to 350, the mixture is a water-white viscous oil-like liquid; d=0.965-0.970; $n_D^{25}$ about 1.404; viscosity about 60,000 centistokes (and said-antifoaming agent is described in U.S. Pat. No. 2,441,098) used in amount of from 0.001 to 0.02% by weight and preferably 0.02% by weight of formulation.

Gel formulations containing a formula I anthranilonitrile of this invention are prepared by mixing either of the above gellant phases and the aqueous solution for one-half hour to two hours under reduced pressure of from 10 to 100 mm Hg and preferably 25 to 50 mm Hg at ambient temperatures of from 20° to 60° C., without the requirements of either additional heating or cooling. This procedure gives an air-free gel which is suitable for administering exact dosages of the antilipogenic composition by volume.

Pellets for subcutaneous injection can be prepared by mixing a formula I anthranilonitrile or related compound or a pharmacologically acceptable salt thereof with a suitable diluent, such as montan wax, carbowax, carnauba wax or the like, and compressing the same into a pellet form. A lubricant such as magnesium or calcium stearate can be added to improve the pelleting process if so desired.

To obtain drug levels necessary to increase growth promotion, improve the carcass quality of meat animals and/or improved the efficiency of feed utilization thereby, it may be necessary to administer multiple pellets to the animal being treated. Moreover, in order to maintain proper drug levels during the treatment period, it may be necessary to administer additional implants to the animals during the treatment period.

While the $R_1$ function of the anthranilonitriles and related compounds of the present invention, represented by formula I above, has been defined as ethyl, n-propyl, isopropyl, t-butyl, 2-butyl, cyclobutyl or cyclopentyl; it is contemplated that compounds of formula I, wherein $R_1$ is

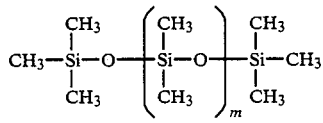

and $R_5$ is $C_3$-$C_5$ alkyl, benzyl or phenethyl; will be effective agents for increasing the growth rate of animals, improving the lean meat to fat ratio thereof and/or improving the efficiency of feed utilization thereby.

The following non-limiting examples further serve to illustrate the invention.

EXAMPLE 1

Preparation of 4-amino-3-bromo-2-fluoroacetophenone and 4-amino-3-bromo-6-fluoroacetophenone A sample of 3-fluoroacetanilide (200 g, 1.31 mole) is mixed with 518 g of aluminum chloride and, while stirred, 184 mL of acetyl chloride is slowly added to give an exotherm. The temperature rises from room temperature to 75° C. and the mixture is maintained at 53° to 70° C. during the addition. The mixture is then heated to 90° to 100° C. and after four hours of reaction time, 500 g of ice and 800 mL of concentrated HCl in 1200 mL of ice/H₂O is added to afford an exotherm. The temperature of the mixture rises to 90° C., is cooled to 30° C. and extracted with 1500 mL of $CH_2Cl_2$. A second extraction of the aqueous layer is performed and the combined extracts are washed with 2×1 L of H₂O, 1 L of saturated Na₂CO₃ solution and 1 L of H₂O. After drying over MgSO₄, the $CH_2Cl_2$ solution is evaporated in vacuo to afford 167 g of 2-fluoro-4-acetamidoacetophenone. This compound (83.5 g) is hydrolyzed with 936 mL of 10% aqueous HCl in 2 L of MeOH for six hours under reflux temperature. The mixture is evaporated to remove MeOH to afford a volume of approximately 900 mL. The mixture which then contains some solid is poured into 500 g of ice and 400 mL of 25% aqueous NaOH solution. The acetophenone is then extracted with 1 L of $CH_2Cl_2$. An additional 25 mL of 25% NaOH solution is added to dissolve solids in the aqueous layer and the mixture is further extracted with $3\times 660$ mL of $CH_2Cl_2$. The combined extracts are washed with $3\times 1$ L of $H_2O$, dried over $Na_2SO_4$ and concentrated to afford 4-amino-2-fluoroacetophenone, mp 110°–112° C. This acetophenone (72.6 g) is dissolved in 2.8 L of $CH_2Cl_2$ and 84.5 g of N-bromosuccinimide is added portionwise at 5°–10° C. After 0.5 hour at 10° C., the mixture is mixed with 1 L of $H_2O$ and the $CH_2Cl_2$ layer is separated and evaporated to dryness to afford 124.2 g of solid. This solid (25 g) is purified by flash chromatography over silica gel using $CH_2Cl_2$ as eluant to afford 10 g of 4-amino-3-bromo-2-fluoroacetophenone, mp 101°–104° C., and 5 g of 4-amino-3-bromo-6-fluoroacetophenone, mp 114°–118° C. Mass spectral analyses indicated molecular weights were 232.

EXAMPLE 2

Preparation of 4-amino-3-cyano-2-fluoroacetophenone

In 128 mL of DMF, 32 g of 4-amino-3-bromo-2-fluoroacetophenone is stirred with 16 g of CuCN at reflux temperature under $N_2$ for 5.5 hours. After cooling, 100 mL of $H_2O$ and 28 g of NaCN are added, the mixture is heated to 80° to 90° C. for 0.5 hour and poured into 600 mL of $H_2O$. The aqueous mixture is stirred for two hours and filtered to collect a brown solid. The solid is stirred in 900 mL of $CH_2Cl_2$ and 100 mL of 10% aqueous NaCN solution. The insoluble solid is filtered and the $CH_2Cl_2$ solution is separated and washed with $3\times 200$ mL of $H_2O$. The $CH_2Cl_2$ solution is decolorized and dried over $Na_2SO_4$. The insoluble brown solid is warmed in 700 mL of EtOAc, stirred, and filtered. The EtOAc solution is diluted with 100 mL of EtOAc, decolorized and dried over $Na_2SO_4$. Both EtOAc and $CH_2Cl_2$ solutions are combined and evaporated in vacuo to afford a brown solid. The solid is triturated with 100 mL of $CH_2Cl_2$ and the mixture is cooled for 15 minutes and filtered to afford 9.8 g of brown solid, mp 133°–139° C., which is identified by NMR to be the title compound.

EXAMPLE 3

Preparation of 5-[2-(tert-butylamino)-1-hydroxyethyl]-6-fluoroanthranilonitrile

In 270 mL of EtOAc, 9 g of 4-amino-3-cyano-2-fluoroacetophenone and 22.6 g of $CuBr_2$ are heated at reflux temperature for 110 minutes. The hot mixture is filtered and the filter cake is washed with 100 mL of EtOAc. The filtrate is evaporated to dryness to afford 12.4 g of brown solid, which is dissolved in 170 mL of THF. The THF solution is washed with $3\times 90$ mL of 20% aqueous $NH_4Cl$ solution, decolorized with charcoal and evaporated to dryness to afford 12.5 g of yellow solid. This solid (10.3 g) is dissolved in 250 mL of EtOH with 122 mL of t-butyl amine under $N_2$ at 10° C. and 5.5 g of $NaBH_4$ is added over ten minutes. The mixture is stirred for 40 minutes at 10° C. and for 20 minutes at 24° C. Water (450 mL) is then added and the mixture is stirred one hour and the EtOH is removed by evaporation in vacuo. The aqueous mixture is then extracted with 400 mL of $CH_2Cl_2$ and then extracted with 100 mL of $CH_2Cl_2$. The combined $CH_2Cl_2$ extracts are washed with $H_2O$ ($2\times 250$ mL), dried over $Na_2SO_4$, decolorized with charcoal, filtered and evaporated to dryness to afford a yellow foam. This material is dissolved in 600 mL of $CH_2Cl_2$ and the solution is extracted with $3\times 300$ mL of aqueous HCl (pH 6). The aqueous extracts are washed with $2\times 200$ mL of $CH_2Cl_2$ and made alkaline (pH 9) with aqueous 10% NaOH solution to afford a precipitate, which is extracted with 300 mL of $CH_2Cl_2$. The $CH_2Cl_2$ solution is washed with $2\times 200$ mL of $H_2O$ and evaporated to dryness. The residue is dissolved in 100 mL of MeOH and 200 mL of acetonitrile and stripped to afford a pale-yellow oil. This oil is dissolved in 200 mL of $H_2O$ containing HCl at pH 3, the solution is adjusted to pH 5 and extracted with $5\times 240$ mL of $CH_2Cl_2$. The aqueous solution is further adjusted to pH 6, 7, 8 and 9 and at each pH level extracted with $5\times 200$ mL of $CH_2Cl_2$. The $CH_2Cl_2$ solutions were evaporated to dryness and the title compound is obtained from extracts from pH 7 and 8. The fractions are dissolved in EtOH, decolorized with charcoal and evaporated to dryness. The fraction from pH 8 melts at 150°–151° C.;

Anal. Calcd. for $C_{13}H_{18}N_3OF$: C, 62.08; H, 7.16; N, 16.71; F, 7.56. Found: C, 62.21; H, 7.32; N, 16.70; F, 7.56.

EXAMPLE 4

In a similar manner as described in Example 3, the following compounds are prepared by substituting the appropriate amine for t-butyl amine:

$$NH_2-\underset{CN\ F}{\underset{|}{\bigcirc}}-\overset{OH}{\underset{|}{C}}HCH_2NHR_1$$

| $R_1$ |
|---|
| Ethyl |
| n-Propyl |
| i-Propyl |
| 2-Butyl |
| Cyclobutyl |
| Cyclopentyl |

EXAMPLE 5

Preparation of 5-[2-(tert-butylamino)-1-hydroxyethyl]-6-fluoro-N,N-dipropylanthranilonitrile In 100 mL of propionic acid, 2 g of 5-[tert-butylamino)-1-hydroxyethyl]-6-fluoroanthranilonitrile is dissolved and 7.5 g of $NaBH_4$ pellets is added to maintain the temperature at 65° C. The mixture is stirred at 65° C. for 48 hours, cooled and made alkaline with NaOH solution. The aqueous mixture is extracted with $CH_2Cl_2$ and the extract is dried over $Na_2SO_4$ and evaporated to dryness. The residue is chromatographed over silica gel using 20% methanolic $CH_2Cl_2$ with 1% aqueous ammonium hydroxide as eluant to afford the title compound after removal of solvent.

EXAMPLE 6

Preparation of
5-[2-(tert-butylamino)-1-hydroxyethyl]-6-fluoro-N-methylanthranilonitrile In 40 mL of dry formic acid, 1.35 g of 5-[(tert-butylamino)-1-hydroxyethyl]-6-fluoroanthranilonitrile is dissolved and the solution is cooled to 5° C. while 3 g of NaBH₄ pellets is added gradually. After an hour, the mixture is made alkaline with aqueous NaOH solution and extracted with CH₂Cl₂. The extract is dried over NaSO₄ and evaporated to dryness. The residue is then chromatographed to afford the monomethylated title product A and the dimethylated product B, by using 20% methanolic CH₂Cl₂ with 1% NH₄OH solution and removal of solvent.

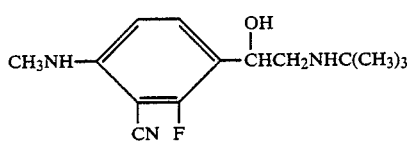

(A)

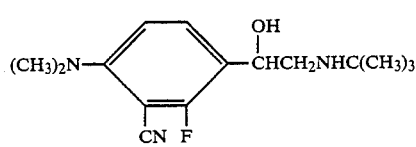

(B)

EXAMPLE 7

The following compounds are obtained by using the procedure of Example 5 and substituting propionic acid with the appropriate acid.

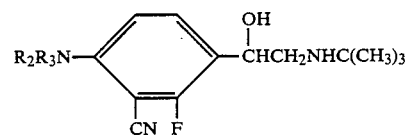

| $R_2$ | $R_3$ |
|---|---|
| CH₃ | CH₃ |
| C₂H₅ | C₂H₅ |

EXAMPLE 8

The following compounds are prepared by modifying the temperature and substituting the appropriate acid for formic acid in Example 6.

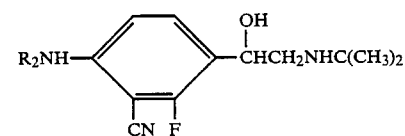

| $R_2$ |
|---|
| C₂H₅— |
| n-C₃H₇— |
| i-C₃H₇— |

EXAMPLE 9

Preparation of
4-amino-3-bromo-2,5-difluoroacetophenone

In the manner described in Example 1, 2,5-difluoroacetanilide is converted to the title compound, which is used as is.

EXAMPLE 10

Preparation of
4-amino-3-cyano-2,5-difluoroacetophenone

In the manner described in Example 2, 4-amino-3-bromo-2,5-difluoroacetophenone is converted to the title compound, which is used as is.

EXAMPLE 11

Preparation of
5-[2-(tert-butylamino)-1-hydroxyethyl]-3,6-difluoroanthranilonitrile and homologs In the manner described in Example 3, the following compounds are prepared using 4-amino-3-cyano-2,5-difluoroacetophenone as starting material:

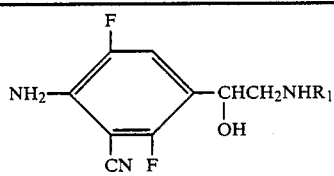

| $R_1$ |
|---|
| Ethyl |
| n-propyl |
| i-propyl |
| t-butyl |
| cyclobutyl |
| cyclopentyl |
| 2-butyl |

EXAMPLE 12

Evaluation of test compounds as antilipogenic agents—mouse tests

CFI female mice from Carworth Farms are received when they are six-weeks old. They are housed ten to a cage in air-conditioned rooms (22° C. to 25° C.) with automatically controlled lights, 14 hours on and ten hours off. The basal diet used in these studies in Purina Laboratory Chow (see description below) which is supplied ad libitum.

The following is a description of the diet to which the growth-promoting compounds were added.

| DIET Guaranteed Analysis | |
|---|---|
| Crude protein not less than | 23.0% |
| Crude fat not less than | 4.5% |
| Crude fiber not more than | 6.0% |
| Ash not more than | 9.0% |

Ingredients

Meat and bone meal, dried skimmed milk, wheat germ meal, fish meal, animal liver meal, dried beet pulp, ground extruded corn, ground oat grains, soybean meal, dehydrated alfalfa meal, cane molasses, animal fat preserved with BHA, vitamin B₁₂ supplement, calcium pantothenate, choline chloride, folic acid, riboflavin supplement, brewer's dried yeast, thiamin, niacin, vitamin A supplement, D-activated plant sterol, vitamin E supplement, calcium carbonate, dicalcium phosphate, iodized salt, ferric ammonium citrate, iron oxide, manganous oxide, cobalt carbonate, copper oxide, zinc oxide. Water is also allowed ad libitum.

Thirteen days after arrival, the mice are weighed in groups of ten and assigned at random to the different treatments. Each of the treatments is tested in three replicates, i.e., in three cages of ten mice each. There are ten cages of ten control mice each. Drugs are mixed in the diet at the dosage level indicated. Feed and water are offered ad libitum for a 12-day test period. Feed spilled is collected during the test period. At the end of the test period, the collected feed is weighed, and the mean feed consumption per cage of ten mice is determined for each treatment. The mice are weighed as a group of ten, and the weight gain determined. The mice are sacrificed by cervical dislocation. The right uterine fat pad of each mouse is removed. The fat pads for each cage of ten mice are weighed as a unit. Reduction in fat pad weights of animals is generally indicative of a reduction of total body fat of the treated animals.

Moreover, when a significant decrease in body fat is coupled with a marked improvement in weight gain in the treated animals, we have found that the lean meat to fat ratio of said-treated animals is substantially improved.

Data obtained are reported in Table I below.

TABLE I

Antilipogenic evaluation of test compounds - mouse study

| Compound | Dosage (ppm) | % Reduction in fat pad weight vs controls | % Change in body weight vs controls | gain (g) |
|---|---|---|---|---|
| Untreated control | — | — | — | 18.5 |
| 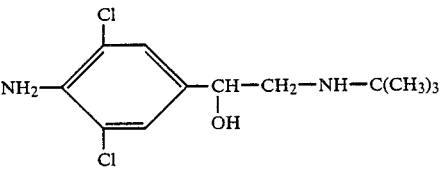 Clenbuterol (U.S. Pat. No. 4,407,819) | 200<br>100<br>50 | −53.66<br>−40.19<br>−22.94 | +2.70<br>+28.65<br>+42.70 | 19.0<br>23.8<br>26.4 |
| 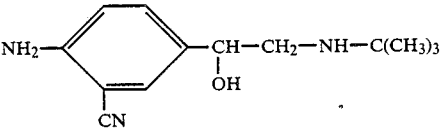 (U.S. Pat. No. 4,407,819) | 200<br>100<br>50 | −64.31<br>−54.62<br>−46.84 | +38.03<br>+54.59<br>+78.92 | 25.7<br>28.6<br>33.1 |
| 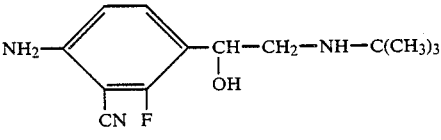 Invention | 200<br>100<br>50 | −67.59<br>−60.67<br>−62.72 | +45.41<br>+47.03<br>+31.35 | 26.9<br>27.2<br>24.3 |

TABLE IA

Antilipogenic evaluation of test compounds - mouse study

| Compound | Dosage (ppm) | % Reduction in fat pad weight vs controls | % Change in body weight vs controls | gain (g) |
|---|---|---|---|---|
| Untreated control | — | — | — | 19.6 |
| 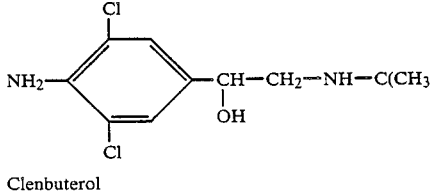 Clenbuterol (U.S. Pat. No. 4,407,819) | 200<br>100<br>50<br>25 | −51.07<br>−28.78<br>−26.44<br>−27.54 | 16.33<br>31.63<br>29.59<br>57.65 | 22.8<br>25.8<br>25.4<br>30.9 |

TABLE IA-continued

Antilipogenic evaluation of test compounds - mouse study

| Compound | Dosage (ppm) | % Reduction in fat pad weight vs controls | % Change in body weight vs controls | gain (g) |
|---|---|---|---|---|
| $NH_2$—⌬(F,F)—CH(OH)—$CH_2$—NH—$C(CH_3)_3$ | 200 | −54.45 | 53.57 | 30.1 |
|  | 100 | −43.93 | 61.22 | 31.6 |
|  | 50 | −21.68 | 48.98 | 29.2 |

TABLE IB

Antilipogenic evaluation of test compounds - mouse study

| Compound | Dosage (ppm) | % Reduction in fat pad weight vs controls | % Change in body weight vs controls | gain (g) |
|---|---|---|---|---|
| Untreated control | — | — | — | 26.7 |
| $NH_2$—⌬(Cl,Cl)—CH(OH)—$CH_2$—NH—$C(CH_3)_3$ | 200 | −52.34 | 42.32 | 38.0 |
|  | 100 | −29.22 | 33.33 | 35.6 |
|  | 50 | −28.48 | 55.43 | 41.5 |
|  | 25 | −15.12 | 16.48 | 31.10 |
|  | 12.5 | −12.38 | 41.20 | 37.7 |
|  | 6.25 | −9.68 | 32.21 | 35.3 |
|  | 3.125 | −17.21 | 45.32 | 38.8 |
| Clenbuterol (U.S. Pat. No. 4,407,819) |  |  |  |  |
| ⌬(F,CN)—CH(OH)—$CH_2$—NH—$C(CH_3)_3$ | 200 | −44.96 | 3.37 | 27.6 |
|  | 100 | −7.95 | 32.21 | 35.3 |
|  | 50 | −13.52 | 21.72 | 32.5 |
|  | 25 | −15.04 | 14.61 | 30.6 |
|  | 12.5 | −3.28 | 11.61 | 29.8 |
|  | 6.25 | −2.58 | 27.72 | 34.1 |
|  | 3.125 | −1.56 | 4.49 | 27.9 |
| ⌬(F,CN,F)—CH(OH)—$CH_2$—NH—$C(CH_3)_3$ | 200 | −47.25 | 25.84 | 33.6 |
|  | 100 | −51.84 | 28.84 | 34.4 |
|  | 50 | −38.77 | 23.60 | 33.0 |
|  | 25 | −27.01 | 32.21 | 35.3 |
|  | 12.5 | −18.24 | 34.08 | 35.8 |
|  | 6.25 | −27.34 | 32.21 | 35.3 |
|  | 3.125 | −17.99 | 34.08 | 35.8 |
| $NH_2$—⌬(CN)—CH(OH)—$CH_2$—NH—$C(CH_3)_2$H | 200 | −65.53 | 17.60 | 31.4 |
|  | 100 | −50.04 | 33.33 | 35.6 |
|  | 50 | −41.11 | 48.31 | 39.6 |
|  | 25 | −21.84 | 38.20 | 36.9 |
|  | 12.5 | −13.69 | 29.21 | 34.5 |
|  | 6.25 | −14.55 | 38.58 | 37.0 |
|  | 3.125 | −20.82 | 29.96 | 34.7 |

From the above data it can be seen that the compound of the invention exhibits substantial improvement in antilipogenic activity over the art compounds against which it was evaluated.

EXAMPLE 13

Measurement of the rate of lipolysis in 3T3-F442A cells

The rate of hydrolysis of the cellular triacylglycerols catalyzed by drug sensitive lipase was measured by the appearance of the radioactivity of $^{14}$C-fatty acid and $^{14}$C-glycerol in the medium after one hour incubation of differentiated 3T3-F442A adipocyte cultures with a test compound.

The 3T3-F442A pre-adipocyte cell line was routinely propagated and grown to confluency in 24-well culture plates in Dulbecco's modified Eagle's medium (DMEM) supplemented with 10% fetal calf serum and penicillin-streptomycin solution (50 units each per one mL medium) at 37° C. in a humidified atmosphere of 10% $CO_2$ in air. The cells were then fed twice with 0.5 mL of the above medium (designated as culture medium) containing 0.8 μg of bovine insulin. The cells differentiated into adipocytes in seven days. Two days prior to conducting experiments, the adipocyte cultures were given fresh culture medium without insulin. On the experiment day, the cultures in the wells were incubated with 7.5 mL of the 2-$^{14}$C-acetate stock solution (10 mM, specific activity 2.5 μCi/μmole) in $CO_2$ incubator for one hour at 37° C. During the labeling period the cells incorporated the labeled acetate into cellular triacylglycerols. The labeled adipocyte cultures were washed twice with DMEM to remove excess labeled acetae. Immediately after the second wash, the cultures received 0.5 mL culture medium. Aliquots of a solution containing a test compound ranging from 0.06 μM to 6 μM concentration were added to the cultures. The cultures were incubated in the $CO_2$ incubator at 37° C. for one hour. Immediately after incubation, two 0.1 mL aliquots of the medium from each well were transferred to vials containing 10 mL of aquasol-2 scintillation solution and assayed for radioactivity. Samples were counted until 40,000 counts had accumulated (1% error at the 95% confidence level) or ten minutes, which ever came first. Radioactivity in dpm was obtained using the counting efficiency from the external standard ratio. Total radioactivity in each individual wells was calculated by multiplying the observed radioactivity in dpm by five. The stimulatory activity is calculated by dividing the radioactivity in the treatment samples over that in the control which had an average of 2680±150 ppm per well.

Two kinetic constants, Vs (maximal stimulation of the rate of lipolysis over control) and Ks (concentration required to achieve a 50% stimulation of the Vs value) were obtained from the Lineweaver-Burk plots of the data generated from the studies of the concentration dependent response to test compounds. These two constants are used to evaluate the rank of potency of the compounds. Cimaterol is a reference compound which has a Vs value of 2.32 and a Ks value of 0.25 μM. A summary of the Vs and Ks values for other compounds is presented in Table II below.

TABLE II

| Rates of lipolysis and effective concentrations for lipolysis in 3T3-F442A cell cultures | | |
|---|---|---|
| Compound | Vs | Ks (μm) |
| $NH_2$—⟨ring, CN, F⟩—$CHCH_2NHC(CH_3)_3$, OH | 2.59 | 0.10 |
| Compound of the invention<br>$NH_2$—⟨ring, F, CN⟩—$CHCH_2NHC(CH_3)_3$, OH | 2.43 | 0.19 |
| Compound C (U.S. Pat. No. 4,119,710 and U.S. Pat. No. 4,407,819)<br>$NH_2$—⟨ring, CN⟩—$CHCH_2NHCH(CH_3)_2$, OH | 2.32 | 0.25 |
| (U.S. Pat. No. 4,119,710 disclosed and U.S. Pat. No. 4,407,819)<br>$NH_2$—⟨ring, CN⟩—$CHCH_2NHC(CH_3)_3$, OH | 1.75 | 0.67 |
| Compound D (U.S. Pat. No. 4,119,710 disclosed | | |

TABLE II-continued

| Rates of lipolysis and effective concentrations for lipolysis in 3T3-F442A cell cultures | | |
|---|---|---|
| Compound | Vs | Ks (μm) |
| and U.S. Pat. No. 4,407,819) | | |

Where Vs is defined as maximum stimulation of the rate of lipolysis over control and Ks is the micromolar (μM) concentration required for achieving 50% of the maximal rate of lipolysis.

EXAMPLE 14

Preparation of 4-bromo-2,5-difluoroaniline

To a stirred solution of 100 g of 2,5-difluoroaniline and 1150 mL of AcOH is added over 1.3 hours a solution of 40.2 mL of $Br_2$ in 350 mL of AcOH at a temperature of 15°–20°. The pink suspension is stirred 30 minutes longer and then evaporated in vacuo. The residue is basified with 50% NaOH (ice is added to keep the temperature below 35°). Extraction of the free base with 1 L of $CH_2Cl_2$ and washing of the extract with 2×100 mL of $H_2O$, drying with $Na_2SO_4$ and evaporation in vacuo gives 157 g (97.5% yield) of 4-bromo-2,5-difluoroaniline, m.p. 73°–75°. The mass spectrum had a M+1 ions at 208,210.

EXAMPLE 15

Preparation of 4-amino-2,5-difluorobenzonitrile

A stirred mixture of 157 g of 4-bromo-2,5-difluoroaniline, 70.15 g of CuCN and 1750 mL of DMF is heated at reflux 7 hours under $N_2$. The cooled solution is treated with 1750 mL of 10% aqueous NaCN and 20 minutes later 3 L of $H_2O$ is added. The black solution is extracted 3 times with $CH_2Cl_2$ (total volume 3.5 L). The organic extract is washed with $H_2O$, saturated $NaHCO_3$, $H_2O$ (500 mL each) and stripped in vacuo. to afford 139.87 g of black oil. The oil is purified on a 75×1500 mm $SiO_2$ dry column using $CH_2Cl_2$ as the eluent to afford 99.68 g (85.7% yield) of 4-amino-2,5-difluorobenzonitrile. A sample is recrystallized from $CH_2Cl_2$/hexane to furnish light tan crystals m.p. 95°–98° C.

Anal. Calcd. for $C_7H_4F_2N_2$: C, 54.54; H, 2.62; N, 18.18. Found: C, 54.62; H, 2.69; N, 18.25.

The mass spectrum had a M+1 ion at 155.

EXAMPLE 16

Preparation of 4-amino-3-bromo-2,5-difluorobenzonitrile

A mixture of 1.65 mL of $Br_2$, 2 mL of $H_2O$ and 5 g of 4-amino-2,5-difluorobenzonitrile in 50 mL of AcOH is stirred at 20°–25° for 16 hours. The solvents are removed in vacuo and the residue partitioned between 100 mL of $H_2O$ and 3×200 ml of $CH_2Cl_2$. The $CH_2Cl_2$ extracts are washed with $H_2O$, saturated $NaHCO_3$, $H_2O$ (100 mL each), dried with $Na_2SO_4$ and evaporated in vacuo to give 6.89 g of crude 4-amino-3-bromo-2,5-difluorobenzonitrile. This is purified by dry-column chromatography using $SiO_2$ to give 5.38 g (71% yield). Recrystallization from $CH_2Cl_2$/hexane affords analytically pure material, m.p. 106°–108° C.

Anal. Calcd. for $C_7H_3BrF_2N_2$: C, 36.08, H, 1.3; N, 12.02. Found: C, 36.08; H, 1.23; N, 12.04.

EXAMPLE 17

Preparation of 4-amino-3-bromo-2,5-difluorobenzaldehyde

A stirred mixture of 30 g of 4-amino-3-bromo-2,5-difluorobenzonitrile, 40 g of Raney nickel and 450 mL of 95–97% HCOOH is heated at 75°–85° C. for 1 hour. The hot solution is filtered through diatomaceous earth filter and the cake washed with 2×200 ml of $CH_2Cl_2$. The total filtrate is stripped in vacuo and the residue treated with excess saturated $NaHCO_3$ and 500 mL of $CH_2Cl_2$. Further extraction with 2×200 mL of $CH_2Cl_2$ is followed by washing the $CH_2Cl_2$ extracts with saturated $NaHCO_3$, 2×$H_2O$ (200 mL each), drying with $Na_2SO_4$ and evaporating in vacuo to furnish 28.25 g of crude 4-amino-3-bromo-2,5-difluorobenzaldehyde. The crude product is purified by dry-column chromatography on silica gel using $CH_2Cl_2$ as eluent to give 20.15 g (66% yield), m.p. 132°–133° C., of the title compound.

Anal. Calcd. for $C_7H_4BrF_2NO$; C, 35.62; H, 1.71; N, 5.93. Found: C, 35.47; H, 1.63; N, 5.85.

EXAMPLE 18

Preparation of 3-bromo-2,5-difluorobenzaldehyde

A mixture of 16 g of 4-amino-3-bromo-2,5-difluorobenzaldehyde and 375 mL of AcOH is stirred until homogenous and 188 mL of 50–52% aqueous hypophosphorous acid is added. Next a solution of 6.8 g of $NaNO_2$ in 38 mL of $H_2O$ is added dropwise over 15 minutes with ice cooling to maintain a temperature of 15°–20° C. The ice bath is removed and stirring continued for 1 hour. the reaction mixture is poured into 1 L of ice/$H_2O$ and extracted with 3×300 mL of $CH_2Cl_2$. The $CH_2Cl_2$ extracts are washed with $H_2O$, 2×10% NaOH, and 2×$H_2O$ (250 mL each), dried with $Na_2SO_4$ and concentrated in vacuo to give 13.32 g (80% yield) of 3-bromo-2,5-difluorobenzaldehyde, m.p. 36°–38° C. Recrystallization from $Et_2O$/hexane furnishes the title compound melting at 37°–40° C. with M+1 ions at 221 and 223 in the mass spectrum.

EXAMPLE 19

Preparation of 3-bromo-2,5-difluoro-α-methylbenzyl alcohol

To a stirred mixture of 13.3 g of 3-bromo-2,5-difluorobenzaldehyde and 300 mL of THF cooled to −35°/−20° under an $N_2$ atmosphere is added 30 mL of 2.85M of MeMgBr in $Et_2O$ over 10 minutes. The cooling bath is removed and the mixture stirred 1 hour and finally poured into 1 L of ice/$H_2O$. 10% HCl is added to bring the pH to ~2 and the mixture extracted with 3×200 ml of $CH_2Cl_2$. The $CH_2Cl_2$ extracts are washed with $H_2O$, saturated $NaHCO_3$, $H_2O$ (250 mL each) and stripped to furnish 14.5 g of crude 3-bromo-2,5-difluoro-α-methylbenzyl alcohol. M+1 ions are observed at 236 and 238 in the mass spectrum. The crude material is used directly in the next step.

EXAMPLE 20

Preparation of 2,5-difluoro-3-(1-hydroxyethyl)-benzonitrile

A mixture of 9.39 g of 3-bromo-2,5-difluoro-α-methylbenzyl alcohol, 3.82 g of CuCN and 117 mL of DMF is stirred and heated at reflux for 7 hours under $N_2$. When the mixture has cooled, 100 mL of 5% aqueous NaCN is added followed by 350 mL of $H_2O$ 30 minutes later. The black solution is extracted with 4×150 mL of $CH_2Cl_2$ and these combined extracts washed with $H_2O$, saturated $NaHCO_3$ and $H_2O$ (150 mL each) and stripped in vacuo to furnish 6.92 g (95% yield) of 2,5-difluoro-3-(1-hydroxyethyl)-benzonitrile as a brown oil. The product exhibits an M+1 ion at 184 in the mass spectrum and appropriate infrared and N.M.R. spectral data.

EXAMPLE 21

Preparation of 3-acetyl-2,5-difluorobenzonitrile

To a stirred mixture of 11.6 of 2,5-difluoro-3-(1-hydroxyethyl)-benzonitrile and 290 mL of acetone is added dropwise over 1 hour 90.5 mL of Kilianis' chromic acid (Fieser and Fieser "Reagents for Organic Synthesis" Vol I p 144) at a temperature of 23°–27°. The mixture is stirred 3.5 hours at 25° C. then poured onto 1 L of ice/$H_2O$ containing 20 g of $Na_2S_2O_5$ and extracted with 4×250 mL of $CH_2Cl_2$. The $CH_2Cl_2$ extracts are washed with $H_2O$, saturated $NaHCO_3$, $H_2O$ (250 mL each) and then evaporated in vacuo. The orange residue is stirred with 10 mL of $Et_2O$ and 40 mL of hexane for 16 hours, filtered and washed with 10 mL of hexane to give 6.85 g (59% yield) of 3-acetyl-2,5-difluorobenzonitrile, m.p. 80°–83° C. The mass spectrum has an M+1 ion at 182.

EXAMPLE 22

Preparation of 3-bromoacetyl-2,5-difluorobenzonitrile

To a stirred mixture of 6.85 g of 3-acetyl-2,5-difluorobenzonitrile and 220 mL of $CHCl_3$ heated at reflux is added dropwise over 75 minutes a solution of 2.1 mL of $Br_2$ in 50 mL of $CHCl_3$. The mixture is boiled for another 15 minutes, cooled to 25° C., washed sequentially with saturated $NaHCO_3$ and $H_2O$ (200 mL each), dried with $Na_2SO_4$ and stripped in vacuo to 10.26 g of brown oil. The oil which contains 78% of 3-bromoacetyl-2,5-difluorobenzonitrile by NMR analysis is satisfactory for the next step.

EXAMPLE 23

Preparation of 3-(2-bromo-1-hydroxyethyl)-2,5-difluorobenzonitrile

To a stirred solution of 10.26 g of crude 3-bromoacetyl-2,5-difluorobenzonitrile in 185 mL of MeOH cooled in ice and under $N_2$ is added 1.48 g of $NaBH_4$. 45 Minutes later, 10% HCl is added until pH 4 is reached. The MeOH is evaporated in vacuo and the residue partitioned between 100 mL of saturated $NaHCO_3$ and 3×50 mL of $CH_2Cl_2$. The combined $CH_2Cl_2$ extracts are washed with 100 mL of $H_2O$, dried with $Na_2SO_4$ and stripped to give 10.23 g of 3-(2-bromo-1-hydroxyethyl)-2,5-difluorobenzonitrile as a brown oil with M+1 ions at 262 and 264 in the mass spectrum.

EXAMPLE 24

Preparation of 3-[2-(tert-butylamino)-1-hydroxyethyl]-2,5-difluorobenzonitrile A stirred mixture of 10.2 g of 3-(2-bromo-1-hydroxyethyl)-2,5-difluorobenzonitrile, 100 mL of t-butylamine and 100 mL of EtOH is heated at reflux under $N_2$ for 2 hours. The mixture is stripped in vacuo and the residue is partitioned between 50 mL of $H_2O$ and 100 mL of 10% NaOH and 3×100 mL of $CH_2Cl_2$. The $CH_2Cl_2$ layers are combined, washed with 2×50 mL of $H_2O$, dried with $Na_2SO_4$ and evaporated in vacuo to afford 9.44 g of partly crystallized dark orange material. This material is dissolved in 100 mL of $CH_2Cl_2$ and extracted with 50 mL of 10% aqueous HCl, 50 mL of $H_2O$, 50 mL of 10% HCl and 50 mL of $H_2O$. The combined aqueous acidic extracts are basified with 10% aqueous NaOH in ice and extracted with $3\times100$ mL of $CH_2Cl_2$. The $CH_2Cl_2$ extracts are washed with $2\times50$ mL of $H_2O$, dried with $Na_2SO_4$ and stripped in vacuo to give an off-white solid. Recrystallization from hexane gives 5.8 g of 3-[2-(tert-butylamino)-1-hydroxyethyl]-2,5-difluorobenzonitrile, m.p. 99°–101° C. The mass spectrum shows an M+1 ion at 255. Infrared and NMR spectral data are consistent.

By substituting isopropylamine for t-butylamine, 3-[2-(isopropylamino-1-hydroxyethyl]-2,5-difluorobenzonitrile is prepared.

EXAMPLE 25

The following compounds are prepared using the procedure of Example 24 and replacing t-butylamine with the appropriate amines:

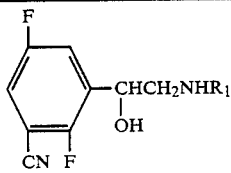

| $R_1$ | Mp °C. |
|---|---|
| $C_2H_5$ | 96–98 |
| i-$C_3H_7$ | 100–102 |
| n-$C_3H_7$ | |
| t-$C_4H_9$ | |
| Cyclobutyl | |
| Cyclopentyl | |

EXAMPLE 26

Preparation of 4-amino-3-bromo-2,5-difluoroacetophenone

To a stirred solution of 20 g of 4-amino-3-bromo-2,5-difluorobenzaldehyde and 400 mL of THF under an $N_2$ atmosphere and cooled in ice is added 60 mL of an 2.85M ethereal solution of MeMgBr. The addition is carried out over 15 minutes at a temperature of 10°–16° C. 80 minutes later another 40 mL of MeMgBr is added and the ice bath is removed. 2 hours later the mixture is poured into 1 L of ice/$H_2O$ and 10% HCl is added to pH 4. The mixture is extracted with $3\times300$ mL of $CH_2Cl_2$. The extracts are washed with $2\times150$ mL of $H_2O$, dried with $Na_2SO_4$ and stripped in vacuo to give 21.76 g of crude 4-amino-3-bromo-2,5-difluoro-α-methylbenzyl alcohol with M+1 ions at 252 and 254 in the mass spectrum.

To a stirred solution of 20.83 g of the benzyl alcohol in 1 L of $CH_2Cl_2$ is added 19.5 g of finely ground pyridinium chlorochromate (PCC) in portions over 10 minutes. 25 Minutes later another 13.3 g of PCC is added and stirring continued for another 90 minutes. The supernatant is decanted off and the residual black tar washed with 100 mL of $CH_2Cl_2$. The combined $CH_2Cl_2$ solutions are washed with $2\times150$ mL of saturated $NaHCO_3$ and $2\times150$ mL $H_2O$, dried with $Na_2SO_4$ and evaporated in vacuo to furnish 18.03 g of a dark solid. The solid is purified on a $SiO_2$ dry column using $CH_2Cl_2$ for elution to give 13.68 g (66% yield) of 4-amino-3-bromo-2,5-difluoroacetophenone with M+1 peaks at 250 and 252 in the mass spectrum.

EXAMPLE 27

Preparation of 3-acetyl-6-amino-2,5-difluorobenzonitrile

A stirred mixture of 12.15 g of 4-amino-3-bromo-2,5-difluoroacetophenone, 133 mL of dimethylformamide and 4.74 g of CuCN is heated at reflux under $N_2$ for 7 hours. When the dark solution has cooled to 22° C., 133 mL of 10% aqueous NaCN is added and the mixture stirred 15 minutes. 250 mL of $H_2O$ is added followed by extraction with $4\times250$ mL of $CH_2Cl_2$. The combined extracts are washed with $H_2O$, saturated $NaHCO_3$ and $H_2O$ (50 mL each) and stripped in vacuo to give 12 g of dark semi-solid. This is applied to a $SiO_2$ dry column and the title compound (5.18 g, 54%) eluted with $CH_2Cl_2$. After slurrying with 25 mL of $Et_2O$, there is obtained 4.04 g of 3-acetyl-6-amino-2,5-difluorobenzonitrile, m.p. 182°–184° C., with an M+1 ion in the mass spectrum at 197.

EXAMPLE 28

Preparation of 5-[2-(tert-butylamino)-1-hydroxyethyl]-3,6-difluoroanthranilonitrile A stirred mixture of 4 g of 3-acetyl-6-amino-2,5-difluorobenzonitrile, 2.51 g of $SeO_2$, 0.72 mL of $H_2O$ and 50 mL of dioxane is heated at reflux under $N_2$ for 6 hours. The Se is filtered off and 5.1 mL of t-$BuNH_2$ added to the ice cold filtrate with stirring under $N_2$. 15 minutes later 300 mL of EtOH is added, followed by 5.1 g of $NaBH_4$ to the cold (10° C.) solution. The reaction is allowed to gradually warm to 25° C. and then stirred 16 hours at this temperature. 300 mL of $H_2O$ is added, the mixture is stirred 2 hours and the bulk of the solvent is removed in vacuo. The residue is extracted with $3\times200$ mL of $CH_2Cl_2$ and the extracts washed with $2\times100$ mL of $H_2O$, dried with $Na_2SO_4$ and evaporated in vacuo. The residue is recrystallized from a small volume of $CH_3CN$ thus providing 2.7 g (49% yield) of the title compound as pink crystals. Recrystallization from $CH_3CN$ and filtration to remove Se finally affords 2.0 g of white crystals m.p. 138°–140°. The mass spectrum shows an M+1 ion at 270.

Anal Calcd. for $C_{13}H_{17}F_2N_3O$: C, 57.98; H, 6.36; N, 15.6. Found: C, 58.66, H, 6.07; N, 15.5.

Similarly, by substituting t-butylamine with isopropylamine, 5-[2-(isopropylamino)-1-hydroxyethyl]-3,6-difluoroanthranilonitrile is prepared.

EXAMPLE 29

Preparation of 4-amino-2,3-difluorobenzonitrile

To a stirred mixture of 50 g of 2,3-difluoroaniline and 1 L of AcOH is added a solution of 20 mL of $Br_2$ in 450 mL of AcOH at a temperature of 15°–20° C. over a period of 2.7 hours. The reaction mixture is stirred for another 1 hour and then the AcOH evaporated in vacuo. The residue is adjusted to pH 11 with 50% NaOH then extracted three times with $CH_2Cl_2$ (total volume used 1 L). The organic extract is washed with $H_2O$ ($2\times100$ mL), dried with $Na_2SO_4$ and concentrated in vacuo to furnish 76.46 g of partly crystalline material which is impure 4-bromo-2,3-difluoroaniline.

A stirred mixture of the crude 4-bromo-2,3-difluoroaniline, 36 g of cuprous cyanide and 908 mL of DMF is heated 7 hours at reflux under an $N_2$ atmosphere. After cooling, 900 mL of 10% aqueous NaCN is added and 45 minutes later 2 L of $H_2O$. The black solution is extracted three times with $CH_2Cl_2$ (total volume 4 L). The $CH_2CL_2$ extract is washed with $H_2O$, saturated $NaHCO_3$ and $H_2O$ (500 mL of each) and then stripped in vacuo. The resulting black oil is purified by dry-column chromatography on silica gel using $CH_2CL_2$ as eluent. There is obtained 31.17 g (55% overall yield) of 4-amino-2,3-difluorobenzonitrile, m.p. 108°–110° C., with the expected ion at 156 in the mass spectrum and consistent NMR and IR spectral data.

EXAMPLE 30

Preparation of 4'-cyano-2',3'-difluoroacetanilide

A mixture of 9.59 g of 4-amino-2,3-difluorobenzonitrile and 20 mL of $Ac_2O$ is heated for 1 hour on a steam bath. The red solution is cooled in an ice bath and the resulting faint pink crystals filtered off, washed with 2×10 mL of $Et_2O$ and air dried. In this manner there is obtained 8.26 g (67% yield) of 4'-cyano-2',3'-difluoroacetanilide, m.p. 175°–177° C. with the appropriate NMR and IR spectral data and an ion at 197 in the mass spectrum.

EXAMPLE 31

Preparation of 2',3'-difluoro-4'-formylacetanilide

A mixture of 11 g of Raney nickel, 8.2 g of 4'-cyano-2',3'-difluoroacetanilide and 125 mL of 95% HCOOH is stirred and heated 30 minutes at 80°–85° C. The hot solution is filtered through diatomaceous earth and the cake washed with 3×100 mL of $CH_2CL_2$. The filtrate and wash are evaporated in vacuo to furnish a white solid. Excess saturated $NaHCO_3$ is added to neutralize the residual HCOOH and the product is extracted with 3×400 mL of $CH_2Cl_2$. The $CH_2Cl_2$ extract is washed with saturated $NaHCO_3$ and $H_2O$ (100 mL each), dried with $Na_2SO_4$ and evaporated to furnish 7.7 g (92.5% yield) of 2',3'-difluoro-4'-formylacetanilide, m.p. 154° C. The mass spectrum shows an ion at 200.

EXAMPLE 32

Preparation of 4'-acetyl-2',3'-difluoroacetanilide

To a stirred solution of 7.7 g of 2',3'-difluoro-4'-formylacetanilide in 190 mL of THF under an $N_2$ atmosphere is added 29 mL of a 2.85M solution of MeMgBr at a temperature of 10°–20° C. The thick suspension is stirred 20 minutes at 20°–25° C., cooled to 15° C. and 5 mL of AcOH cautiously added. The mixture is then poured onto 500 mL of ice/$H_2O$ and the product extracted into 500 mL of $CH_2CL_2$. This extract is washed with $H_2O$, saturated $NaHCO_3$ and $H_2O$ (100 mL each) and stripped to give 8.1 g of yellow gummy 2',3'-difluoro-4'-(1-hydroxyethyl)-acetanilide. 8.1 g of the crude 2',3'-difluoro-4'-(1-hydroxyethyl)-acetanilide is stirred in acetone (175 mL) while 54 mL of Kilianis' reagent (Fieser and Fieser, "Reagents for Organic Synthesis", Vol. I p144) is added dropwise during 30 min. at a temperature of 20°–25° C. After stirring 30 min. longer, the reaction mixture is poured onto 200 mL of ice/$H_2O$ containing 5 g of $Na_2S_2O_5$. The green suspension is extracted three times with $CH_2Cl_2$ (total volume 1 L) and the organic extract is washed with $H_2O$, saturated $NaHCO_3$, $H_2O$ (100 mL each) and stripped in vacuo. There is obtained 5.8 g of off-white solid which is slurried with 75 mL of $Et_2O$ to afford 5.23 g (65% yield) of 4'-acetyl-2',3'-difluoroacetanilide, m.p. 149°–152° C., (Mass spectrum shows an ion of 214).

EXAMPLE 33

Preparation of 4'-[2-(tert-butylamino)-1-hydroxyethyl]-2',3'-difluoroacetanilide A stirred mixture of 2.87 g of $SeO_2$, 0.8 mL of $H_2O$, 4.89 g of 4'-acetyl-2',3'-difluoroacetanilide and 60 mL of dioxane is heated at reflux for 6 hours under $N_2$. The black Se is filtered off and washed with 10 mL of dioxane. To the stirred dioxane filtrate and wash is added 5.75 mL of t-butylamine (some cooling is used to maintain a temperature of 20°–25° C.). After stirring an additional 20 min., 345 mL of EtOH is added and the mixture cooled to 10° C. 5.7 g of $NaBH_4$ is added in portions over 20 minutes and the mixture is stirred 15 hours at 20°–25° C. 350 mL of $H_2O$ is run in and stirring is continued for 4 hours. The solvents are removed in vacuo and 50 mL $H_2O$ is added followed by extraction with 3×300 mL of $CH_2Cl_2$. The organic extracts are washed with $H_2O$ (50 mL + 100 mL), dried with anhydrous $Na_2SO_4$ and stripped in vacuo to afford 4.82 g (73.8% yield) of 4'-[2-(tert-butylamino)-1-hydroxyethyl]-2',3'-difluoroacetanilide as a white foam with an M+1 ion at 287 in the mass spectrum and consistent IR and NMR spectral data.

EXAMPLE 34

Preparation of 4-amino-α-[(tert-butylamino)methyl]-2,3-difluorobenzyl alcohol

A stirred mixture of 4.82 g of 4'-[2-tert-butylamino)-1-hydroxyethyl]-2',3'-difluoroacetanilide, 50 mL of EtOH and 50 mL of 10% aqueous NaOH is heated at reflux for 4 hours under $N_2$. The bulk of the solvents are distilled out under vacuum and the tan residue is collected, washed with $H_2O$ (3×50 mL) and air dried. Recrystallization from $CH_3CN$ affords 2.42 g (58% yield) of 4-amino-α-[(tert-butylamino)methyl]-2,3-difluorobenzyl alcohol, m.p. 133°–135° C.

Anal. Calcd. for $C_{12}H_{18}F_2N_2O$: C, 59.00; H, 7.43; N, 11.47. Found: C, 59.42; H, 7.45; N, 11.56.

The mass spectrum showed an M+1 ion at 245.

Similarly, by using the procedure of Example 33 and replacing t-butylamine with isopropylamine and continuing with the procedure of Example 34, 4-amino-α-[(isopropylamino)methyl]-2,3-difluorobenzyl alcohol is prepared.

EXAMPLE 35

α-[(tert-butylamino)methyl]-2,3-difluorobenzyl alcohol

By using the procedure of Example 18, 4-amino-α-[(tert-butylamino)methyl]-2,3-difluorobenzyl alcohol is deaminated with $H_3PO_2$ to afford the title compound. Similarly, 2,3-difluoro-α-[(isopropylamino)methyl]benzyl alcohol is obtained from its corresponding 4-amino compound.

EXAMPLE 36

4-Acetyl-2-chloro-5-fluoroacetanilide

To a 250 mL flask fitted with a magnetic stirring bar, thermometer and a $N_2$ inlet/outlet is added under $N_2$ 5.0 g (25.60 mmoles) of 4-acetyl-3-fluoroacetanilide, 2.5 mL of 12N HCl, 35 mL of HOAc and 0.08 g of AIBN. The flask is cooled to 5° C. with an ice bath and a solution of 1.15 g of sodium chlorate in 6.0 mL of water is added over a 10 minute period. The red color immediately turns to a yellow color. After 5 minutes, a precipitate forms and the reaction is stirred for 3 hours at 5° C. Then 90 mL of water is added to precipitate more solid. After cooling in an ice bath for 30 minutes, the solid is filtered off under vacuum and washed with 30 mL of water. The solid is air dried to yield 1.65 g of slightly yellow solid, which is the title compound.

EXAMPLE 37

4-Acetyl-2-chloro-5-fluoroaniline

A sample (0.5 g) of 4-acetyl-2-chloro-5-fluoroacetanilide is hydrolyzed by heating in 5.6 mL of 10% aqueous HCl and 12 mL of MeOH at reflux for an hour. The mixture is evaporated to near dryness, diluted with 30 mL of H$_2$O to precipitate solids and filtered. The filter cake is washed well with H$_2$O and dried to afford 0.25 g of the title compound, m.p. 97°–98° C.

EXAMPLE 38

4-Acetyl-2-chloro-5-fluoro-6-iodoaniline

In 4.8 mL of HOAc, 0.5 g of 4-acetyl-2-chloro-5-fluoroaniline and 0.47 g of HgO are stirred under N$_2$. At room temperature over 4 hours, 0.79 g of I$_2$ is added and after stirring an additional hour, the mixture is filtered and the filter cake washed with 3 mL of AcOH To the filtrate and washed solution, 75 mL of H$_2$O is added to precipitate the title compound, which is collected, washed with H$_2$O and air dried to afford 0.83 g, m.p. 117°–119° C.

EXAMPLE 39

4-Acetyl-2-chloro-6-cyano-5-fluoroaniline

In 2.5 mL of DMF, 0.5 g of 4-acetyl-2-chloro-5-fluoro-6-iodoaniline and 0.15 g of CuCN are heated at 130° C. for 4 hours. The mixture is cooled and 20 mL of H$_2$O is added and stirring is continued for 0.5 hour. The precipitate is collected, washed with water, boiled in 50 mL of MeOH for 10 minutes and filtered. The MeOH filtrate is concentrated to give 0.32 g of the title compound, m.p. 180°–182° C.

EXAMPLE 40

3-Cyano-5-chloro-2-fluoroacetophenone

In the manner described in Example 18, 4-acetyl-2-chloro-6-cyano-5-fluoroaniline is deaminated with H$_3$PO$_2$ to afford the title compound, m.p. 91°–93° C.

EXAMPLE 41

3-[(2-(test-butylamino)-1-hydroxyethyl]-5-chloro-2-fluorobenzonitrile hydrochloride Using the procedure of Example 33, 3-cyano-5-chloro-2-fluoroacetophenone is oxidized, reductively aminated and converted to the hydrochloride salt with methanolic HCl to afford the title compound, m.p. 233°–235° C.

Replacement of t-BuNH$_2$ with i-PrNH$_2$ in the reductive amination step of the above procedure affords 3-[1-hydroxyethyl-2-(isopropylamino)]-5-chloro-2-fluorobenzonitrile hydrochloride.

EXAMPLE 42

4-Acetyl-2,6-dichloro-3-fluoroaniline

In 10 mL of toluene, 0.5 g of 4-acetyl-2-chloro-5-fluoroaniline and 0.42 g of N-chlorosuccinimide are heated at reflux for several hours until the reaction is complete. The mixture is filtered and the filter cake is washed with H$_2$O. The filtrate of the original reaction mixture is concentrated to afford a precipitate which is collected and washed with H$_2$O. The solids are combined to afford the crude title compound, which is used further as is.

EXAMPLE 43

4-Acetyl-2-bromo-6-chloro-3-fluoroaniline

In the manner described in Example 41, 4-acetyl-2-bromo-3-fluoroacetophenone is chlorinated to afford the title compound.

EXAMPLE 44

Using the procedure of Example 33, the following compounds are prepared using the appropriate substituted acetophenones and amines:

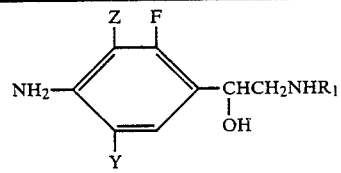

| R$_1$ | Z | Y |
|---|---|---|
| t-butyl | Cl | Cl |
| Isopropyl | Cl | Cl |
| t-butyl | Cl | Br |
| Isopropyl | Cl | Br |
| Ethyl | Cl | Cl |
| t-butyl | CN | Cl |
| t-butyl | Cl | CH$_3$ |

EXAMPLE 45

Using the method of Example 18, the compounds of Example 44 are deaminated to give the following compounds:

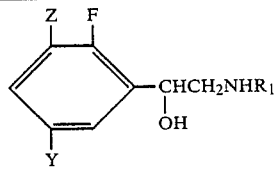

| R$_1$ | Z | Y |
|---|---|---|
| t-Butyl | Cl | Cl |
| Isopropyl | Cl | Cl |
| t-Butyl | Cl | Br |
| Isopropyl | Cl | Br |
| Ethyl | Cl | Cl |
| t-Butyl | CN | CH$_3$ |
| Isopropyl | CN | CH$_3$ |
| t-Butyl | CN | Cl |
| t-Butyl | Cl | CH$_3$ |

EXAMPLE 46

4-Bromo-3-fluoro-6-methylaniline

Using the procedure of Example 14, 3-fluoro-6-methylaniline is brominated to afford the title compound.

EXAMPLE 47

4-Amino-2-fluoro-5-methylbenzonitrile

Using the method of Example 15, 4-bromo-3-fluoro-6-methylaniline is converted into the title compound.

EXAMPLE 48

4-Amino-3-bromo-2-fluoro-5-methylbenzonitrile

Using the method of Example 14, 4-amino-2-fluoro-5-methylbenzonitrile is brominated to afford the title compound.

EXAMPLE 49

4-Amino-3-bromo-2-fluoro-5-methylbenzaldehyde

Using the method of Example 17, 4-amino-3-bromo-2-fluoro-5-methylbenzonitrile is converted into the title compound.

EXAMPLE 50

4-Amino-3-bromo-2-fluoro-5,α-dimethylbenzyl alcohol

Using the method of Example 19, 4-amino-3-bromo-2-fluoro-5-methylbenzaldehyde is reacted with MeMgBr to afford the title compound.

EXAMPLE 51

2-Amino-3-methyl-6-fluoro-5-(1-hydroxyethyl)-benzonitrile

Using the method of Example 15, 4-amino-3-bromo-2-fluoro-5,α-dimethylbenzyl alcohol is converted into the title compound using CuCN.

EXAMPLE 52

5-Acetyl-2-Amino-6-fluoro-3-methylbenzonitrile

Using the method of Example 21, 2-amino-3-methyl-6-fluoro-5(1-hydroxyethyl)benzonitrile is oxidized to afford the title compound.

EXAMPLE 53

2-Amino-6-fluoro-5-[2-(tert-butylamino)-1-hydroxyethyl]-m-tolunitrile

Using the procedure of Example 27, 2-amino-3-methyl-6-fluoro-5-(1-hydroxyethyl)benzonitrile is converted into the title compound.

In the same manner 2-amino-6-fluoro-5-[2-isopropylamino-1-hydroxyethyl]-m-tolunitrile is prepared by replacing t-butylamine with isopropylamine.

EXAMPLE 54

The following compounds are prepared by the method of Example 5 by using the appropriate acid(s) in the reductive alkylation.

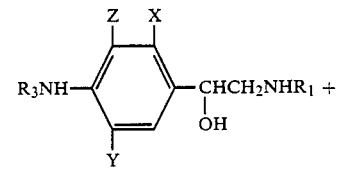

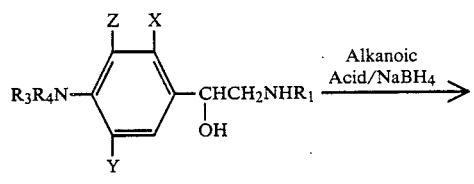

(where R₃ = R₄)

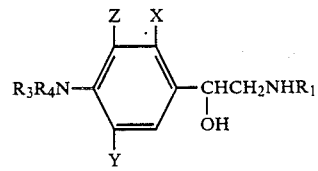

(where R₃ = R₄)

| X | Z | Y | R₁ | R₃ | R₄ |
|---|---|---|---|---|---|
| F | CN | F | t-butyl | CH₃ | C₂H₅ |
| F | CN | F | i-propyl | CH₃ | C₂H₅ |
| F | F | H | t-butyl | CH₃ | C₂H₅ |
| F | CN | CH₃ | t-butyl | CH₃ | C₂H₅ |
| F | CN | CH₃ | i-propyl | CH₃ | C₂H₅ |
| F | CN | Cl | t-butyl | CH₃ | C₂H₅ |
| F | Cl | Cl | t-butyl | CH₃ | n-C₃H₅ |

EXAMPLE 55

Preparation of 5-acetyl-6-chloroanthranilonitrile

A mixture of 4'-amino-3'-bromo-2'-chloroacetophenone (17 g, 58 mmol) and cuprous cyanide (5.2 g, 58 mmol) is warmed in DMF (85 mL) to 80°–100° C. for 6 hours, then poured into H₂O (1.5 L), stirred for 15 minutes and filtered. The brown solid was washed with H₂O (200 mL) and then boiled in EtOAc (500 mL) and filtered. This extraction is repeated. The EtOAc filtrate is washed twice with 20% NH₄Cl (500 ml), twice with H₂O (500 mL), dried with Na₂SO₄, and evaporated to give a brown solid. After flash column chromatography (SiO₂, EtOAc-CH₂Cl₂, 1:20), the product is isolated as a yellow solid; yld. 5.5 g (48%); m.p. 189°–193° C.

EXAMPLE 56

Preparation of 5-(bromoacetyl)-6-chloroanthranilonitrile

Cupric bromide (4.5 g, 0.02 mol) and 5-acetyl-6-chloroanthranilonitrile (2 g, 0.01 mol) are heated at reflux in EtOAc (100 mL) and CHCl₃ (100 mL) for 2½ hours and then filtered hot. The brown solid is washed with EtOAc (20 mL) and the filtrate is evaporated. The yellow solid residue is taken up into EtOAc (600 mL), washed with H₂O (500 mL) and evaporated. The yellow solid was dried by azeotroping with EtOH; yield 2 g (71%); m.p. 180°–207° d.C.

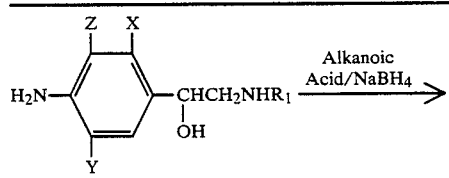

EXAMPLE 57

Preparation of
5-[2-(tert-butylamino)-1-hydroxyethyl]-6-chloroanthranilonitrile

To a stirred solution of t-BuNH$_2$ (30 mL) in absolute EtOH (40 mL) under N$_2$ is added 5-(bromoacetyl)-6-chloroanthranilonitrile (2 g, 7.3 mmol) at 25° C. The mixture is warmed to 43°, and when homogeneous (at 43° C.) the mixture is immediately cooled to 9° C. and NaBH$_4$ (1 g, 26.3 mmol) is added slowly so as to control the evolution of gas. The mixture is stirred for one hour at 9° C. and then for 2 hours at room temperature. Water (75 mL) is added and the mixture is stirred for 30 minutes and decanted from an off-white gum. The solvents are evaporated to give a yellow tar. After flash column chromatography (SiO$_2$, THF-EtOAc, 1:1), the product is isolated as a pale-yellow solid; yld. 0.75 g (38%); m.p. 85°–88° C.

By substituting t-BuNH$_2$ with i-PrNH$_2$, 5-[2-(isopropylamino)-1-hydroxyethyl]-6-chloroanthranilonitrile is obtained.

Deamination of both products by the method of example 18 affords 3-[2-(tert-butylamino)-1-hydroxyethyl]-2-chlorobenzonitrile and 2-chloro-3-[2-(isopropylamino)-1-hydroxyethyl]benzonitrile, respectively.

EXAMPLE 58

Preparation of
4-Acetamido-α-[(tert-butylamino)methyl]-2,5-difluorobenzyl alcohol A stirred mixture of 5 g of 4-acetamido-2,5-difluoroacetophenone, 2.92 g of SeO$_2$, 0.85 mL of H$_2$O and 58 mL of dioxane is heated at reflux under N$_2$ for 6 hours. The black Se is removed by filtration and 6 mL of t-BuNH$_2$ is added to the stirred filtrate with some cooling. After stirring 20 minutes, 310 mL of EtOH is added and the mixture is cooled down to 5°–10° while 5.95 g of NaBH$_4$ is added in 3 portions. After 16 hours, the reaction is worked up by stirring 4 h with 400 mL of H$_2$O and then removing the bulk of the solvent in vacuo and extracting with 4×25 mL of CH$_2$Cl$_2$. The combined organic extracts are washed with 2×200 mL of H$_2$O, dried with anhydrous Na$_2$SO$_4$ and evaporated in vacuo to 5.37 g of a white foam. The foam is crystallized from 25 mL of CH$_3$CN to afford 3.63 (54% yield) of the title compound, m.p. 142°–144° C. The compound exhibits an M+1 ion at 287 in the mass spectrum and has the anticipated NMR and infrared spectral data.

Substitution of t-BuNH$_2$ with isopropylamine affords 4-acetamido-α-[(isopropylamino)methyl]-2,5-difluorobenzyl alcohol.

EXAMPLE 59

Preparation of
4-Amino-α-[(tert-butylamino)methyl]-2,5-difluorobenzyl alcohol

A stirred mixture consisting of 3.6 g of 4-acetamido-α-[(tert-butylamino)methyl]-2,5-difluorobenzyl alcohol, 36 mL of EtOH and 36 mL of 10% aqueous NaOH is heated at reflux under N$_2$ for 4 h. The EtOH is evaporated in vacuo and the residue is extracted with 4×60 mL of CH$_2$Cl$_2$. The combined organic extracts are washed with 25 mL of H$_2$O, dried with anhydrous Na$_2$SO$_4$ and evaporated in vacuo to furnish the title compound which is crystallized from CH$_3$CN/hexane, 2.77 g (90% yield), m.p. 115°–116° C.

Analysis: Calc. for C$_{12}$H$_{18}$F$_2$N$_2$O: C, 59.0; H, 7.43; N, 11.47%. Found: C, 59.36; H, 7.51; N, 11.48%. The compound has an M+1 ion in the mass spectrum at 245 and has consistent infrared and NMR spectral data.

Similarly, 4-amino-α-[(isopropylamino)methyl]-2,5-difluorobenzyl alcohol is obtained by hydrolysis of 4-acetamido-α-[(isopropylamino)methyl]2,5-difluorobenzyl alcohol.

Deamination of the para-amino group of these products by the method of example 18 affords α-[(isopropylamino)methyl]2,5-difluorobenzyl alcohol and α-[(tert-butylamino)methyl]2,5-difluorobenzyl alcohol.

EXAMPLE 60

Preparation of
3-[2-(tert-butylamino)-1-hydroxyethyl]-5-chloro-2-fluorobenzonitrile hydrochloride To a 250 mL round bottom flask fitted with a reflux condenser, under N$_2$, is added 50 mL of dioxane, 0.85 mL of H$_2$O and 2.66 g of SeO$_2$. The mixture is warmed to 60° C. to give a homogeneous solution. Under N$_2$ is added 4.23 g of 3-acetyl-5-chloro-2-fluorobenzonitrile and the dark-colored solution refluxed for 6 hours. The mixture containing a black precipitate is cooled to room temperature and filtered thru diatomaceous earth. The dark-red solution is cooled to 0° C. under N$_2$ and 8.46 mL of tert-butylamine is added over a 15 minute period. The yellow mixture is stirred at room temperature for 16 hours. Then 100 mL of EtOH is added, cooled to 0° C. and 4.65 g of NaBH$_4$ is slowly added over a 30 minute period. The reaction is stirred at room temperature for 4 hours to get a homogeneous solution. Then 100 mL of H$_2$O is added and the mixture stirred for 1.5 hours. The organic solvents are removed under reduced pressure and the remaining aqueous extracted with 3×300 mL of CH$_2$Cl$_2$. The CH$_2$Cl$_2$ extract is washed with 300 mL of H$_2$O, dried over Na$_2$SO$_4$ and filtered. The CH$_2$Cl$_2$ is removed under reduced pressure to give a yellow oil. The oil is dissolved in 50 mL of ether and cooled in an ice bath. A solution of anhydrous HCl in MeOH is added to the ether solution to pH-2. The light yellow solid is filtered off and recrystallized from i-PrOH and ether to give 1.28 g of cream colored solid, m.p. 234°–236° C.

Similarly, 3-(isopropylamino)-1-hydroxyethyl)-5-chloro-2-fluorobenzonitrile is obtained by replacing t-BuNH$_2$ with i-PrNH$_2$.

EXAMPLE 61

5-[2-(tert-butylamino)-1-hydroxyethyl]-3,6-dichloroanthranilonitrile

Using the procedure of example 42, 5-acetyl-6-chloroanthranilonitrile is chlorinated with NCS to afford 5-acetyl-3,6-dichloroanthranilonitrile, which is then converted to 3,6-dichloro-5-[2-(tert-butylamino)-1-hydroethyl]anthranilonitrile by the method of example 59.

Similarly 3,6-dichloro-5-[2-(isopropylamino)-1-hydroxyethyl]anthranilonitrile is prepared by substituting t-butylamine with isopropylamine.

Deamination of the ring amino by the method of example 18 affords 2,5-dichloro-3-[2-(tert-butylamino)-1-hydroxyethyl]benzonitrile and 2,5-dichloro-3-[2-(isopropylamino)-1-hydroxyethyl]benzonitrile.

EXAMPLE 62

Preparation of 3-[2-(tert-butylamino)-1-hydroxyethyl]-2-fluorobenzonitrile

Using the method of example 60, 3-acetyl-2-fluorobenzonitrile is converted to the title compound, m.p. 88°–90° C.

Similarly, 3-[2-(isopropylamino)-1-hydroxyethyl]-2-fluorobenzonitrile is obtained by substituting isopropylamine for t-butylamine.

Reduction of 3-acetyl-5-chloro-2-fluorobenzonitrile in methanol using H$_2$/Pd-C for 3 h under 45 p.s.i.g. of H$_2$ in the presence of triethylamine affords 3-acetyl-2-fluorobenzonitrile, which is the starting material.

What is claimed is:

1. A method for increasing the growth rate, improving feed efficiency or improving the carcass quality by increasing the lean meat to fat ratio of warm-blooded animals, comprising: orally or parenterally administering to said animals an effective amount to achieve at least one of the animal body functions above, of a compound of the formula:

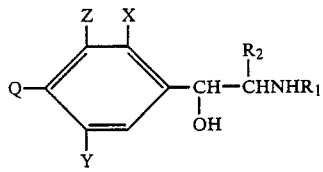

wherein R$_1$ is ethyl, n-propyl, isopropyl, tert-butyl, 2-butyl, cyclobutyl or cyclopentyl; R$_2$ is hydrogen or methyl; X is fluorine or chlorine; Y is hydrogen, methyl, fluorine, chlorine or bromine; Z is hydrogen, fluorine, chlorine or cyano; and Q is hydrogen or; with the provisos that Y and Z cannot simultaneously be hydrogen; and when Z is hydrogen, Y is fluorine or chlorine and X is fluorine; the optical isomer; or the pharmacologically acceptable salt thereof.

2. A method according to claim 1, wherein R$_2$ is hydrogen; and Y is hydrogen, methyl, fluorine or chlorine.

3. A method according to claim 1, wherein R$_2$ is hydrogen; Y is hydrogen, fluorine or chlorine; and Z is hydrogen or cyano.

4. A method according to claim 1, wherein R$_1$ is isopropyl or tert-butyl; R$_2$ is hydrogen; Y is hydrogen, fluorine or chlorine; and Z is hydrogen or cyano.

5. A method according to clain 1, wherein R$_1$ is isopropyl or tert-butyl; R$_2$ is hydrogen; and Y is hydrogen, fluorine or chlorine.

6. A method according to claim 1, wherein the compound is 5-[2-(isopropylamino)-1-hydroxyethyl]-6-fluoroanthranilonitrile.

7. A method according to claim 1, wherein the compound is 5-[2-(tert-butylamino)-1-hydroxyethyl]-3,6-difluoroanthranilonitrile.

8. A method according to claim 1, wherein the compound is 5-[2-(tert-butylamino)-1-hydroxyethyl]-6-chloroanthranilonitrile.

9. A method according to claim 1, wherein the compound is 5-[2-(isopropylamino)-1-hydroxyethyl]-3,6-difluoroanthranilonitrile.

10. A method according to claim 1, wherein the compound is 3-[2-(tert-butylamino)-1-hydroxyethyl]-5-chloro-2-fluorobenzonitrile.

11. A method according to claim 1, wherein said warm-blooded animals are poultry, swine, sheep, goats, cattle or domestic pets, and said compound is orally administered to said animals in a feed containing from about 0.05 to 200 grams of said compound per ton of feed.

12. A method according to claim 1, wherein the compound is 4-amino-α-[(tert-butylamino)methyl]-2,3-difluorobenzyl alcohol.

13. A method according to claim 1, wherein the compound is 3-[2-(tert-butylamino)-1-hydroxyethyl]-2,5-difluorobenzonitrile.

14. A method according to claim 1, wherein the compound is α-[(tert-butylamino)methyl]-2,5-difluorobenzyl alcohol.

15. A method according to claim 1, wherein the compound is α-[(isopropylamino)methyl]-2,5-difluorobenzyl alcohol.

16. A method according to claim 1, wherein the compound is 4-amino-α-[(tert-butylamino)methyl]-2,5-difluorobenzyl alcohol.

17. A method according to claim 1, wherein said warm-blooded animals are poultry, swine, sheep, goats, cattle or domestic pets, and said compound is parenterally administered to said animals by subcutaneous injection of an implant composition containing sufficient compound to provide said animals with from about 0.001 to 100 mg/kg/day of body weight of said compound.

18. An animal feed premix comprising from about 5.0% to 50.0% by weight of 5-[2-(tert-butylamino)-1-hydroxyethyl]-6-fluoroanthranilonitrile; 5-[2-(isopropylamino)-1-hydroxyethyl]-6-fluoroanthranilonitrile; 5-[2-(tert-butylamino)-1-hydroxyethyl]-3,6-difluoroanthranilonitrile; 5-[2-(isopropylamino)-1-hydroxyethyl]-3,6-difluoroanthranilonitrile; 3-[2-(tert-butylamino)-1-hydroxyethyl]-2,5-difluorobenzonitrile; 3-[2-(isopropylamino-1-hydroxyethyl]-2,5-difluorobenzonitrile; α-[(tert-butylamino)methyl]-2,3-difluorobenzyl alcohol; 3-[2-(tert-butylamino)-1-hydroxyethyl]-2-fluorobenzonitrile; α-[(tert-butylamino)methyl]-2,5-difluorobenzyl alcohol; 4-amino-α-[(tert-butylamino)methyl]-2,5-difluorobenzyl alcohol; 4-amino-α-[(tert-butylamino)methyl]-2,3-difluorobenzyl alcohol or a pharmacologically acceptable salt thereof; and from about 50.0% to 95% by weight of an edible diluent selected from corn meal, fish meal, soybean meal, bone meal, alfalfa meal, cottonseed oil meal, urea, molasses or mixtures of one or more of said edible diluents.

19. A compound of formula (I):

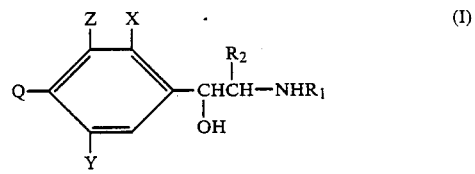

wherein R$_1$ is ethyl, n-propyl, isopropyl, tert-butyl, 2-butyl, cyclobutyl or cyclopentyl; R$_2$ is hydrogen or methyl; X is fluorine or chlorine; Y is hydrogen, methyl, fluorine, chlorine or bromine; Z is hydrogen, fluorine, chlorine or cyano; Q is hydrogen or NH$_2$; with the provisos that Y and Z cannot simultaneously be hydrogen; that when Y is hydrogen, X and Z cannot be chlorine; that when Q is hydrogen, Z is cyano; and that when Z is hydrogen, X is fluorine and Y is fluorine or chlorine; the optical isomer; or the pharmacologically acceptable salt thereof.

20. A compound according to claim 19, wherein $R_2$ is hydrogen; and Y is hydrogen, methyl, fluorine or chlorine.

21. A compound according to claim 19, wherein $R_2$ is hydrogen; and Y is hydrogen, fluorine or chlorine.

22. A compound according to claim 19, wherein $R_1$ is isopropyl or tert-butyl; $R_2$ is hydrogen; and Y is hydrogen, fluorine or chlorine.

23. A compound according to claim 19, wherein $R_1$ is isopropyl or tert-butyl; $R_2$ is hydrogen; and Y is hydrogen, fluorine or chlorine.

24. A compound according to claim 19, 5-[2-(tert-butylamino)-1-hydroxyethyl]-6-fluoroanthranilonitrile.

25. A compound according to claim 19, 5-[2-(isopropylamino)-1-hydroxyethyl]-6-fluoroanthranilonitrile.

26. A compound according to claim 19, 5-[2-(tert-butylamino)-1-hydroxyethyl]-3,6-difluoroanthranilonitrile.

27. A compound according to claim 19, 5-[2-(isopropylamino)-1-hydroxyethyl]-3,6-difluoroanthranilonitrile.

28. A compound according to claim 19, 3-[2-(tert-butylamino)-1-hydroxyethyl]-2,5-difluorobenzonitrile.

29. A compound according to claim 19, 3[2-(isopropylamino-1-hydroxyethyl]-2,5-difluorobenzonitrile.

30. A compound according to claim 19, 5-[2-(tert-butylamino)-1-hydroxyethyl]-6-fluoro-3-methylanthranilonitrile.

31. A compound according to claim 19, 4-amino-α-[(tert-butylamino)methyl]-2,3-difluorobenzyl alcohol.

32. A compound according to claim 19, 3-[2-(tert-butylamino)-1-hydroxyethyl]-5-chloro-2-fluorobenzonitrile hydrochoride.

33. A compound according to claim 19, 4-amino-α-[(tert-butylamino)methyl]-2,5-difluorobenzyl alcohol.

* * * * *

UNITED STATES PATENT OFFICE
CERTIFICATE OF CORRECTION

Patent No. 4,863,959　　　　Dated September 5, 1989

Inventor(s) Terence J. Bentley et al.

It is certified that error appears in the above-identified patent and that said Letters Patent is hereby corrected as shown below:

Claim 1, line 39, after "cyano;", "and" should be deleted. Same line, after "Q is hydrogen or", -- $NH_2$ -- should be inserted.

Claim 1, line 41, after "hydrogen;", "and" should be deleted and -- that -- should be inserted. Same line, after "when", "Z" should be deleted and -- Y -- should be inserted. Same line, after "hydrogen;", the following should be inserted: -- X and Z cannot be chlorine; that when Q is hydrogen, Z is cyano; and that when Z is hydrogen, X is fluorine and --.

Claim 1, line 42, after "chlorine", "and X is fluorine" should be deleted.

Claim 5, line 53, "clain" should be deleted and -- claim -- should be inserted.

Signed and Sealed this

Twenty-ninth Day of October, 1991

Attest:

HARRY F. MANBECK, JR.

Attesting Officer　　　Commissioner of Patents and Trademarks